US007344892B2

(12) United States Patent (10) Patent No.: US 7,344,892 B2
Thadhani et al. (45) Date of Patent: Mar. 18, 2008

(54) SCREENING FOR GESTATIONAL DISORDERS

(75) Inventors: Ravi I. Thadhani, Boston, MA (US); S. Ananth Karumanchi, Chestnut Hill, MA (US)

(73) Assignees: Beth Israel Deaconess Medical Center, Inc., Boston, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 10/947,791

(22) Filed: Sep. 23, 2004

(65) Prior Publication Data

US 2005/0148040 A1 Jul. 7, 2005

Related U.S. Application Data

(60) Provisional application No. 60/505,707, filed on Sep. 23, 2003.

(51) Int. Cl.
*G01N 33/53* (2006.01)
*G01N 33/577* (2006.01)

(52) U.S. Cl. ...................... 436/501; 436/804; 436/809; 435/7.1

(58) Field of Classification Search ...................... None
See application file for complete search history.

(56) References Cited

U.S. PATENT DOCUMENTS

| 5,580,554 | A | 12/1996 | Keith |
| 6,461,830 | B1 | 10/2002 | Parrott |
| 2002/0102530 | A1 | 8/2002 | Keith, Jr. et al. |
| 2002/0110833 | A1 | 8/2002 | Caniggia et al. |

FOREIGN PATENT DOCUMENTS

WO  WO 98/28006  7/1998

OTHER PUBLICATIONS

Moutquin et al. (CMAJ. 1997; 157:907-919).*
Barden et al. Clin Sci (Lond). 1999; 97:475-83.*
Lal et al. Drug Discov Today. Sep. 15, 2002; 18: S143-S148.*
merck.com/mmhe/sec22/ch258/ch258c.html; accessed May 23, 2007; 10 pages.*
Ong et al. Journal Reprod Med. 2004; 49: 477-480.*
Liu et al. Zhonghua Fu Chan Ke Za Zhi. Jan. 2001;36(1):5-8—article in Chinese, translation provided.*
Seely and Solomon, "Insulin Resistance and its Potential Role in Pregnancy-Induced Hypertension," *The Journal of Clinical Endocrinology & Metabolism*, vol. 88(6), pp. 2393-2398, (2003).
Levine et al., "Circulating Angiogenic Factors and the Risk of Preeclampsia," *The New England Journal of Medicine*, vol. 350, pp. 672-683, (2004).
Polliotti et al., "Second-Trimester Maternal Serum Placental Growth Factor and Vascular Endothelial Growth Factor for Predicting Severe, Early-Onset Preeclampsia," *The American College of Obstetricians and Gynecologists*, vol. 101, No. 6, pp. 1266-1274, (2003).
Taylor et al., "Longitudinal Serum Concentrations of Placental Growth Factor: Evidence for Abnormal Placental Angiogenesis in Pathologic Pregnancies," *American Journal Obstetricians and Gynecologists*, vol. 188, pp. 177-182 (2003).
Thadhani et al., "Insulin Resistance and Alternations in Angiogenesis Additive Insults That May Lead to Preeclampsia," *Hypertension*, vol. 43, pp. 988-992, (2004).
Tidwell et al., "Low Material Serum Levels of Placenta Growth Factor as an Antecedent of Clinical Preeclampsia," *American Journal Obstetricians and Gynecologists*, vol. 184, pp. 1267-1272 (2001).
Wolf et al., "First Trimester Insulin Resistance and Subsequent Preeclampsia: A Prospective Study," *The Journal of Clinical Endocrinology & Metabolism*, vol. 87(4), pp. 1563-1568, (2002).
Wolf et al., "Insulin Resistance But Not Inflammation is Associated with Gestational Hypertension," *Hypertension*, vol. 40, pp. 886-891, (2002).
Wolf et al., "Preeclampsia and Future Cardiovascular Disease: Potential Role of Altered Angiogensis and Insulin Resistance," *The Journal of Clinical Endocrinology & Metabolism*, vol. 89(12), pp. 6239-6243, (2004).
Rinehart et al., "Expression of the Placental Cytokines Tumor Necrosis Factor α, Interleukin 1β, and Interleukin 10 is Increased in Preeclampsia," *Am J Obstet Gynecol*, Oct. 1999, pp. 915-920.
Thadhani et al., "First Trimester Placental Growth Factor and Soluble Fms-Like Tyrosine Kinase 1 and Risk for Preeclampsia," *The journal of Clinical Endocrinology & Metabolism*, 89(2), pp. 770-775, (add date).
Maynard et al., "Excess Placental Solube Fms-Like Tyrosine Kinase 1 (sFlt1) may Contribute to Endothelial Dysfunction, Hypertension, and Proteinuria in Preeclampsia," *The Journal of Clinical Investigation*, Mar. 2003, vol. 111, No. 5, pp. 1-10.
Page et al., "Placental Peptides as Markers of Gestational Disease," *Reproduction* (2002) 123, 487-495.
Masséet al., "A Prospective Study of Several Potential Biologic Markers for Early Prediction of the Development of Preeclampsia," *Am J Obstet Gynecol*, vol. 169, No. 3, pp. 501-508.
Heikkinen et al., "Cytokine Levels in Midtrimester Amniotic Fluid in Normal Pregnancy and in the Prediction of Pre-Eclampsia," *Scand. J. Immunol.* 53, 310-314, 2001.
Helske et al., "Expression of Vascular Endothelial Growth Factor Receptors 1, 2 and 3 in Placentas From Normal and Complicated Pregnancies," *Molecular Human Reproduction*, vol. 7, No. 2, pp. 205-210, 2001.
Acromite, "Androgens in preeclampsia," Am. J. Obstet. Gynecol. 180(1 Pt 1):60-3 (1999), abstract only.

(Continued)

*Primary Examiner*—Elizabeth C. Kemmerer
*Assistant Examiner*—Christina Borgeest
(74) *Attorney, Agent, or Firm*—Fish & Richardson P.C.

(57) ABSTRACT

The invention relates to methods and compositions for identifying subjects having, or predisposed to having, gestational diabetes, preeclampsia, and gestational hypertension. The methods are applicable to urine and/or blood samples and can be conducted prior to the third trimester of pregnancy.

15 Claims, 7 Drawing Sheets

OTHER PUBLICATIONS

Izumi et al., "Calcium-to-creatinine ratio in spot urine samples in early pregnancy and its relation to the development of preeclampsia," Metabolism. 46(10):1107-8 (1997), abstract only.

Serin et al., "Androgen levels of preeclamptic patients in the third trimester of pregnancy and six weeks after delivery," Acta Obstet. Gynecol Scand. 80(11):1009-13 (2001), abstract only.

Van den Elzen, "Serum lipids in early pregnancy and risk of pre-eclampsia," Br. J. Obstet. Gynaecol. 103(2):117-22 (1996), abstract only.

Wolf et al., "Obesity and preeclampsia: the potential role of inflammation," Obstet. Gyencol. 98(5 Pt 1):757-62 (2001), abstract only.

* cited by examiner

| +/- I | IL-6 | IL-6+I | IL-8 | IL-8+I | MCP | MCP+I |
|---|---|---|---|---|---|---|
| Patient 1 | 1.3 | 1.0 | 2.6 | 2.6 | 1.6 | 1.5 |
| Patient 2 | 1.0 | 1.1 | 2.1 | 2.0 | 1.9 | 1.9 |
| Patient 3 | 0.8 | 0.8 | 2.5 | 2.7 | 1.5 | 1.4 |
| Patient 4 | 3.3 | 3.5 | 2.2 | 2.0 | 4.3 | 4.3 |
| Patient 5 | 1.1 | 0.9 | 2.5 | 2.7 | 1.5 | 1.3 |

FIG. 3

| Reproducibility | IL-6 (1) | IL-6 (2) | IL-8 (1) | IL-8 (2) | MCP (1) | MCP (2) |
|---|---|---|---|---|---|---|
| Patient 1 | 1.3 | 1.3 | 2.6 | 2.4 | 1.6 | 1.8 |
| Patient 2 | 1.0 | 1.3 | 2.2 | 2.2 | 1.8 | 1.9 |
| Patient 3 | 0.8 | 0.9 | 2.5 | 2.4 | 1.6 | 1.4 |
| Patient 4 | 3.5 | 3.4 | 2.2 | 2.1 | 4.6 | 4.3 |
| Patient 5 | 1.1 | 1.2 | 2.7 | 2.5 | 1.4 | 1.5 |

FIG. 4

| SERUM | PlGF* pg/ml | sFlt-1 pg/ml | Ratio (sFlt-1/PlGF) |
|---|---|---|---|
| Controls | 163 | 478 | 3 |
| GDM | 34 | 723 | 21 |
| PE | 26 | 1176 | 45 |

FIG. 5

| URINE | PlGF* pg/g Cr | IL-6* pg/g Cr | MCP-1* pg/g Cr |
|---|---|---|---|
| PE | 53.7 | 40.7 | 494 |
| Controls | 71.9 | 10.9 | 244 |

*Normalized for urine creatinine

FIG. 6

| Postpartum Pilot | GDM | PE | UP |
|---|---|---|---|
| Age (yrs) | 27 | 33 | 32 |
| BMI (kg/m$^2$) | 27 | 26 | 25 |
| CRP (mg/L) | 1.2 | 1.4 | 0.6 |
| IL-6 (pg/ml) | 2.1 | 1.9 | 1.1 |
| Fasting Glucose (mmol) | 5 | 4.7 | 4.4 |
| Fasting Insulin (pmol/L) | 84 | 84 | 66 |
| HOMA$_{IR}$ | 3.12 | 2.86 | 1.96 |
| $\Delta I_{30}/\Delta G_{30}$ (pmol/mmol) | 104 | 180 | 147 |
| HOMA-IR = (fasting insulin x fasting glucose)/22.5) | | | |
| $\Delta I_{30}/\Delta G_{30}$ (pmol/mmol)-first-phase insulin secretion | | | |

FIG. 7

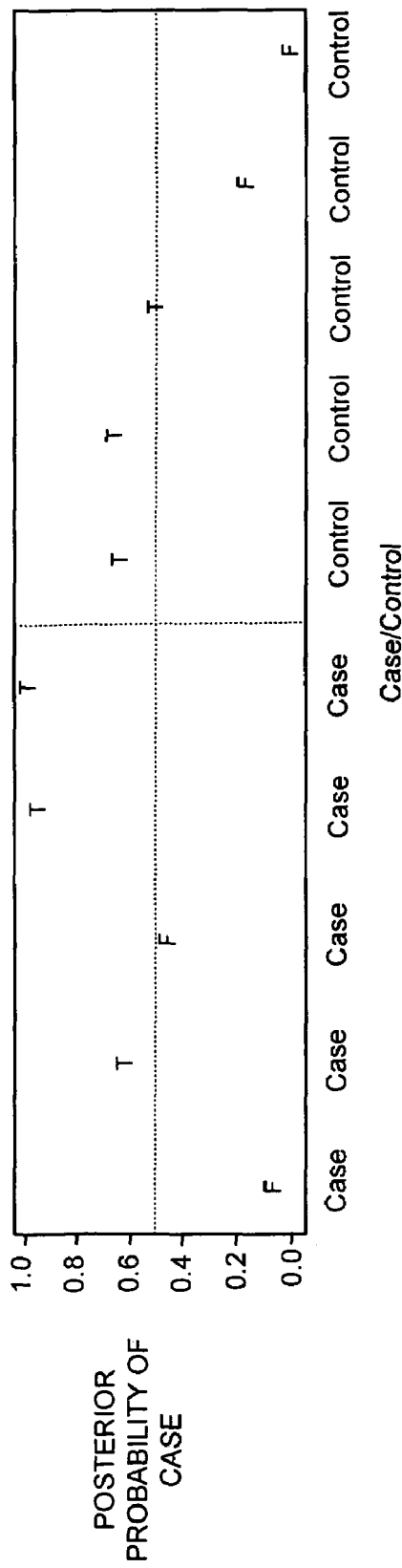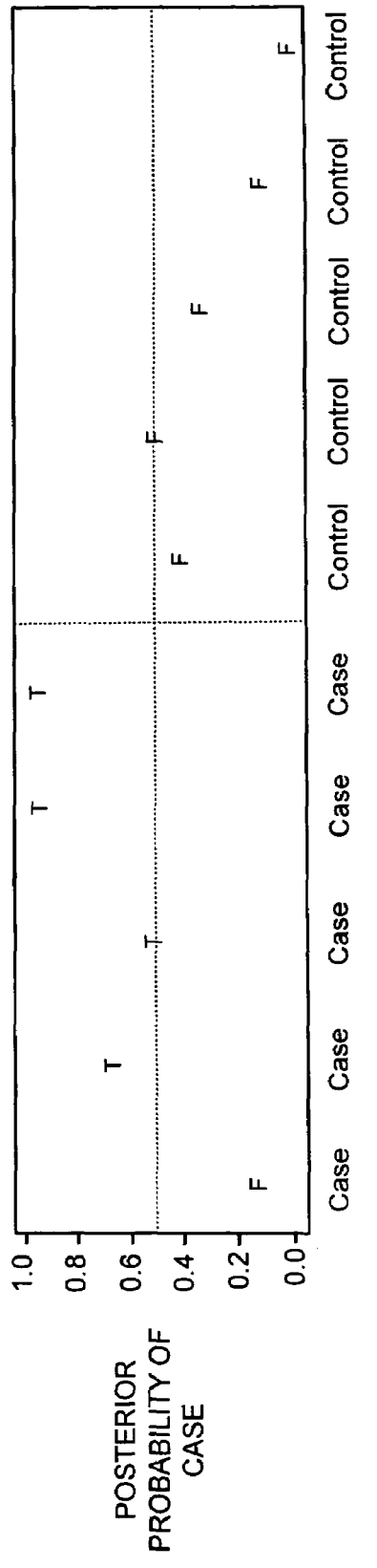
FIG. 9

| Cases:Controls 1:1 | Power | | |
|---|---|---|---|
| SD | 0.75 | 1.0 | 1.25 |
| N=50 | 0.82 | 0.98 | 1.0 |
| N=60 | 0.90 | 1.0 | 1.0 |
| N=70 | 0.95 | 1.0 | 1.0 |

FIG. 10

| Cases:Controls 1:3 | Power | | |
|---|---|---|---|
| RR | 2.5 | 3.0 | 3.5 |
| N=60 | 0.81 | 0.87 | 0.94 |

FIG. 11

SCREENING FOR GESTATIONAL DISORDERS

CROSS-REFERENCE TO RELATED APPLICATION

This application claims priority from U.S. Provisional Patent Application No. 60/505,707, filed on Sep. 23, 2003, the contents of which is incorporated herein by reference in its entirety.

STATEMENT AS TO FEDERALLY SPONSORED RESEARCH

This invention was made with Government support under HD39223 awarded by the National Institutes of Health. Thus, the Government has certain rights in the invention.

TECHNICAL FIELD

This invention relates to screening for gestational disorders, and more particularly to screening for biomarkers present in a biological sample obtained from a pregnant subject that are indicative of a gestational disorder.

BACKGROUND

Gestational diabetes mellitus (GDM) and pregnancy-induced hypertension (PIH) complicate 2-3% and 5-10% of all pregnancies, respectively. These disorders can occur in the third-trimester of pregnancy and are associated with significant maternal and fetal morbidity and mortality. Gestational diabetes has been described as the new onset or new diagnosis of glucose intolerance during pregnancy and is associated with fetal complications relating to macrosomia, such as shoulder dystocia and birth trauma. In addition, GDM is associated with increased cesarean section rates and increased risk of PIH. PIH is associated with preterm labor, increased cesarean section rates, acute renal failure, hepatic dysfunction, stroke, coagulopathy and death. For the fetus, PIH is associated with low birth weight, extended neonatal intensive care and intrauterine death.

PIH-related disorders include preeclampsia (PE) and gestational hypertension (GH). Preeclampsia is characterized as the combination of high blood pressure (hypertension), swelling (edema), and protein in the urine (albuminuria, proteinuria) developing after the 20th week of pregnancy. Preeclampsia ranges in severity from mild to severe; the mild form is sometimes called proteinuric pregnancy-induced hypertension or proteinuric gestational hypertension. Gestational (transient) hypertension is generally characterized as the acute onset of hypertension in pregnancy or the early puerperium without proteinuria or abnormal edema and resolving within 10 days after delivery.

Individuals at increased risk of developing preeclampsia and eclampsia include primigravidas and women with multiple gestations, molar pregnancy or fetal hydrops, chronic hypertension or diabetes, or a personal or family history of eclampsia or preeclampsia. Preeclampsia (PE) and gestational hypertension (GH) are forms of PIH.

The present standard therapy for PIH, including PIH resulting from GDM, is delivery, often at the expense of fetal well-being. Prophylactic strategies to prevent PIH, including calcium supplementation and aspirin therapy, have been mostly unsuccessful. One reason these trials have failed is that the absence of screening tests limits the ability to administer the therapeutic interventions early enough to modify pregnancy outcome. For example, diagnosing PE by the appearance of edema and proteinuria alone is unreliable as edema is common in normal pregnancies and measurable proteinuria usually occurs only after hypertension is manifested. Therefore, such a test lacks specificity and fails to detect GDM or PIH prior to manifestation of the disease in the third trimester of pregnancy.

Currently, no single biochemical marker, or plurality of biochemical markers, reliably identifies women at risk for developing GDM or PIH prior to the third trimester of pregnancy. Thus, there exists a need for diagnostic methods and compositions that lead to early implementation of therapy and improved pregnancy outcomes for women at risk for gestational disorders.

SUMMARY

The invention is based on the discovery that sex hormone binding globulin (SHBG) and/or placental growth factor (PlGF) can be used as early indicators for the risk of developing any of the pregnancy complications preeclampsia, gestational diabetes, and gestational hypertension. The assays for SHBG and PlGF are simple and inexpensive, can be performed during the first trimester as early as 5 weeks after conception, and do not require any preparation on the part of the woman (for example, the tests can be done under fasting or non-fasting conditions). Thus, the invention provides methods for utilizing insulin resistance biomarkers, such as SHBG and cytokines such as interleukin-6 (IL-6), and angiogenic biomarker, such as PlGF and soluble fms-like tyrosine kinase 1 (sFlt1), as indicators of the risk for developing various pregnancy complications.

In general, the invention features methods of determining a woman's risk of developing a gestational disorder, such as preeclampsia, gestational diabetes, and/or gestational hypertension, during pregnancy, by obtaining a biological sample, such as blood or serum, from a pregnant woman during the first or second trimester of pregnancy (e.g., at 5 weeks after conception, or at any time between 6 to 12 weeks, or at 8, 10, 12, 14, 16, 18, 20, or 24 weeks after conception); and measuring the level of sex hormone binding globulin (SHBG), or SHBG and PlGF, in the sample; wherein the level of SHBG, or SHBG and PlGF, in the sample indicates the level of risk of developing preeclampsia, gestational diabetes, or gestational hypertension. In these methods, the sample can be a fasting or non-fasting sample. The new methods can be used to assess the level of risk for all or any one or more of gestational diabetes, gestational hypertension, and preeclampsia. PlGF can also be detected in urine samples.

In certain embodiments, the methods include measuring the level of SHBG in a biological, e.g., serum or blood, sample obtained from the pregnant subject; measuring the level of PlGF in a biological sample, e.g., a serum, blood, or urine sample, obtained from the pregnant subject; comparing the SHBG level obtained from the pregnant subject with an SHBG level obtained from at least one subject having a normal pregnancy; and comparing the PlGF level obtained from the pregnant subject with a PlGF level obtained from at least one subject having a normal pregnancy. A low level of SHBG and PlGF present in the sample obtained from the pregnant subject, as compared to the levels present in the at least one subject having a normal pregnancy, indicates that the pregnant subject has, or is predisposed to having, a gestational disorder.

In another aspect, the SHBG and/or PlGF levels are correlated with: 1) the gestational age at the time SHBG and PlGF levels are measured; 2) the pregnant subject's age; 3) the pregnant subject's parity; and 4) the pregnant subject's body mass index.

In another aspect, the method further includes measuring the level of at least one cytokine or growth factor (or both) in the subject biological sample, e.g., urine, blood, or serum sample, and generating a subject profile comprising a value or plurality of values, each value representing a level of a specific cytokine, SHBG, and/or PlGF, and comparing the subject profile with a reference profile, wherein the reference profile comprises a value or plurality of values, each value representing a level of a specific cytokine, SHBG, and/or PlGF in a reference urine sample obtained from a reference subject. The cytokine can be an immune/hematopoietin, an interferon, a tumor necrosis factor (TNF)-related molecule or a chemokine. Examples include interleukin (IL)-6, IL-8, IL-1β, monocyte chemoattractant protein (MCP)-1 or TNF-α, or any combination thereof. A reference profile can be generated from a sample obtained from any source containing, or believed to contain, a cytokine. References levels of cytokines and/or growth factors can be used to generate reference profiles. For example, the reference profile can be obtained from the urine, serum, plasma, amniotic fluid, or placental tissue of a reference subject. A reference subject can be a pregnant individual having a gestational disorder or a pregnant individual having a normal pregnancy.

The methods of the invention can be accomplished by contacting a sample obtained from a pregnant subject with an array of immobilized biomolecules specific for SHBG and/or PlGF and detecting a modification of the biomolecules. The modification is indicative of the level of SHBG and/or PlGF in a sample and can include stable or transient binding of the biomolecule to SHBG or PlGF. The subject SHBG and PlGF levels can be compared to reference levels obtained from reference subjects. Reference levels can further be used to generate a reference profile from one or more reference subjects. In one aspect, the biomolecules are antibodies, such as monoclonal antibodies. In another aspect, the biomolecules are antigens, such as viral antigens that specifically recognize cytokines. In yet another aspect, the biomolecules are receptors.

In another aspect, the invention features arrays for detecting a gestational disorder. These arrays include a substrate having a plurality of addresses, each address having disposed thereon a set of one or more biomolecules, and each biomolecule in a set specifically detecting the same molecule; wherein a first set of one or more biomolecules specifically detects SHBG, and a second set of one or more biomolecules specifically detects PlGF. The arrays can further include biomolecules that specifically detect cytokines such as, for example, interleukin (IL)-6, IL-8, IL-1β, monocyte chemoattractant protein (MCP)-1 or TNF-α. In one aspect, an array of the invention further includes at least two addresses having disposed thereon an immobilized growth factor-specific biomolecule that specifically detects at least one growth factor, such as, for example, soluble fms-like tyrosine kinase-1 receptor (sFlt-1), vascular endothelial growth factor (VEGF), or fibroblast growth factor (FGF)-2.

The invention also features a pre-packaged diagnostic kit for detecting a gestational disorder. The kit can include an array as described herein and instructions for using the array to test a biological sample, e.g., a urine, blood, or serum sample, to detect a gestational disorder.

The invention also includes methods, e.g., using the new arrays, to determine the efficacy of a therapy administered to treat a gestational disorder. These methods include contacting the array with a sample obtained from a pregnant patient undergoing therapy for a gestational disorder. The level of SHBG and/or PlGF can be determined and compared to the level of SHBG and/or PlGF detected in a sample obtained from the patient prior to, or subsequent to, the administration of the therapy. Subsequently, a caregiver can be provided with the comparison information for further assessment.

Further, a subject profile can be entered into a computer system that contains, or has access to, a database that includes a plurality of digitally-encoded reference profiles. Each profile of the plurality has a plurality of values, each value representing a level of SHBG and/or PlGF of a pregnant individual having, or predisposed to having, a gestational disorder. In this manner, a single subject profile can be used to identify a subject at risk for developing a gestational disorder based upon reference values.

Thus, in other aspects, the invention also features computer-readable media that contain a database including one or more digitally-encoded reference profiles, wherein a first reference profile represents a level of SHBG in one or more samples from one or more pregnant individuals having a gestational disorder, and optionally, a second reference profile that represents a level of PlGF in one or more samples from one or more pregnant individuals having a gestational disorder.

The invention also features computer systems for determining whether a pregnant subject has, or is predisposed to having, a gestational disorder. These systems include a database that has one or more digitally-encoded reference profiles, wherein a first reference profile represents a level of SHBG in one or more samples from one or more pregnant individuals having a gestational disorder, and, optionally, a second reference profile represents a level of PlGF in one or more samples from one or more pregnant individuals having a gestational disorder; and a server that includes a computer-executable code for causing the computer to: i) receive a profile of a pregnant subject comprising a level of SHBG, or the levels of SHBG and PlGF detected in a sample from the subject; ii) identify from the database a matching reference profile that is diagnostically relevant to the pregnant subject profile; and iii) generate an indication of whether of the subject has, or is predisposed to having, a gestational disorder.

In addition to their use to identify women who are at risk, the new methods can be used as a routine screen or "pre-screen" for all pregnant women to identify those women who are not at risk for gestational complications, thus avoiding the need for additional testing later during pregnancy.

As used herein, the terms "biological molecules" and "biomolecules" may be used interchangeably. These terms are meant to be interpreted broadly, and generally encompass polypeptides, peptides, oligosaccharides, polysaccharides, oligopeptides, proteins, oligonucleotides, and polynucleotides. Oligonucleotides and polynucleotides include, for example, DNA and RNA, e.g., in the form of aptamers. Biomolecules also include organic compounds, organometallic compounds, salts of organic and organometallic compounds, saccharides, amino acids, and nucleotides, lipids, carbohydrates, drugs, steroids, lectins, vitamins, minerals, metabolites, cofactors, and coenzymes. Biomolecules further include derivatives of the molecules described. For example, derivatives of biomolecules include lipid and glycosylation derivatives of oligopeptides, polypeptides, peptides, and proteins, such as antibodies. Further examples of derivatives of biomolecules include lipid derivatives of oligosaccharides and polysaccharides, e.g., lipopolysaccharides.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 3 is a table providing data regarding the recovery of cytokines from urine samples in the presence or absence of a protease inhibitor.

FIG. 4 is a table providing data regarding the reproducibility of identifying cytokines in a biological sample using a cytokine array.

FIG. 5 is a table providing data regarding the ratio of sFlt-1/PlGF in the serum of pregnant subjects.

FIG. 6 is a table providing data regarding the correlation of cytokine levels and growth factor levels in the identification of a gestational disorder.

FIG. 7 is a table providing data on serum samples from women with a history of GDM, PE, and normoglycemic/normotensive uncomplicated pregnancy (UP).

FIG. 9 is a graph that depicts the results of a Bayesian discriminant analysis as applied to the data set of 5 proteins (cytokines) measured on each of 5 cases and 5 controls.

FIG. 10 is a table providing the results for detecting mean differences in cytokine levels in case versus control subjects.

FIG. 11 is a table providing the results of a calculation that detects significant linear trends (chi-square test for trend) across tertiles for identifying the relative risk (RR) of a subject in developing a gestational disorder.

DETAILED DESCRIPTION

Figure 1:
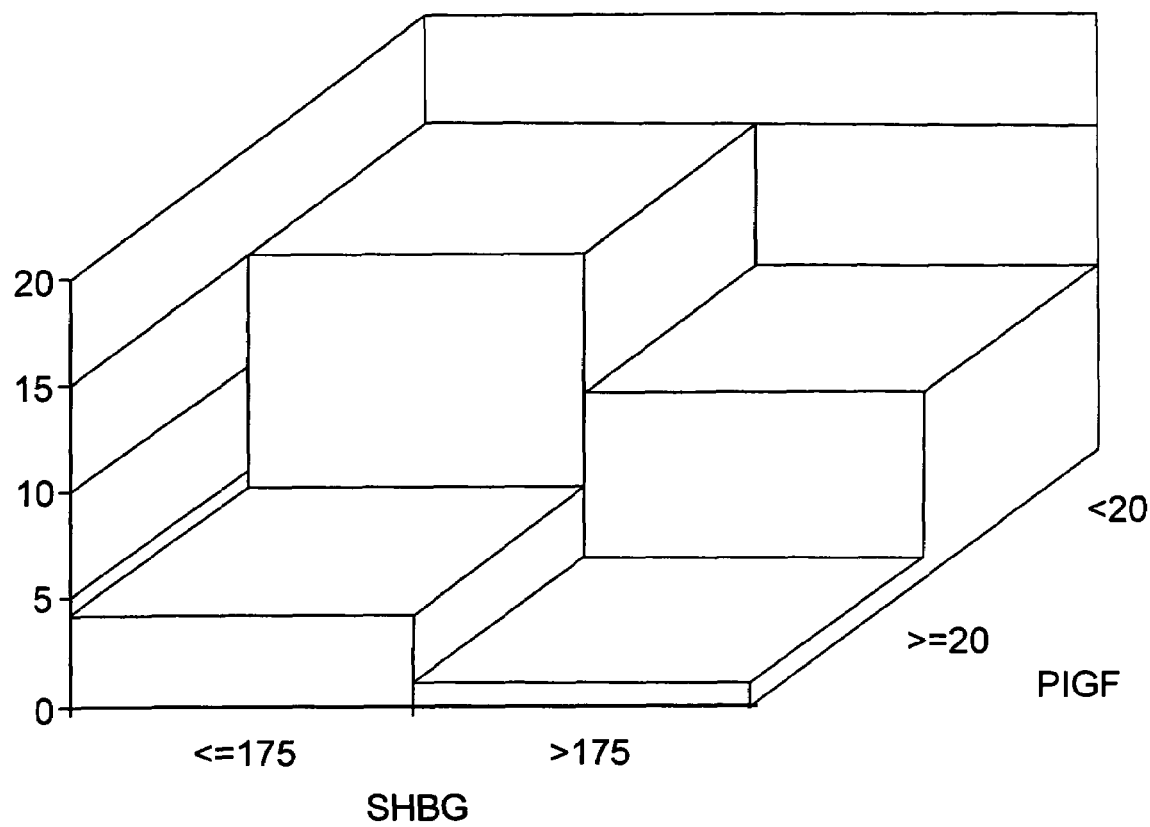
FIG. 1 is a three-dimensional graph of a comparison between PlGF (pg/ml) and SHBG (nmol/L) levels in identifying subjects at risk for developing a gestational disorder.

Gestational disorders such as pregnancy-induced hypertension (PIH) and gestational diabetes mellitus (GDM) occur in the third-trimester of pregnancy and are associated with significant maternal and fetal morbidity and mortality. Currently there are no effective laboratory tests to predict the incidence of either disorder early in pregnancy. Diagnoses are generally made during the third trimester when symptoms arise or during routine blood pressure and blood glucose screening. The critical absence of diagnostic tests to predict these disorders has hindered the ability of investigators to identify preventive therapeutic agents; current preventive strategies have failed in large part because these interventions were initiated late in pregnancy when the possibility to alter pregnancy outcomes is limited. Furthermore, the absence of early predictive markers limits clinicians' ability to implement preventive therapies in high-risk women.

Pre-eclampsia (PE) is an endothelial cell disorder the pathogenesis of which is not well understood. PE has been associated with alterations in expression of angiogenesis-related proteins such that administration of sFlt1, an endogenous inhibitor to vascular endothelial growth factor (VEGF) and placental growth factor (PlGF), resulted in phenotypic similarities to PE in animals. Indeed, low levels of serum PlGF and VEGF (pro-angiogenic) and increased levels of sFlt-1 (anti-angiogenic) appear to antedate onset of clinical symptoms. Thus, as described herein, low levels of PlGF relate to pre-eclampsia.

In addition to alterations in angiogenesis, however, women who develop PE also have evidence of insulin resistance. In-vitro models outside of pregnancy suggest insulin signaling and angiogenesis are intimately related. For example, insulin activates the expression of VEGF mRNA in endothelial cells, and both insulin and VEGF signaling leads to nitric oxide production. The insulin resistance syndrome is comprised of a cluster of metabolic abnormalities that confer increased risk of diabetes, hypertension and cardiovascular disease. Several features of the insulin resistance syndrome, such as obesity, hypertension, dyslipidemia, systemic inflammation, and impaired fibrinolysis, are also associated with preeclampsia. In addition, women with polycystic ovary syndrome or gestational diabetes, two disorders characterized by insulin resistance, are at increased risk of preeclampsia.

Because both normal insulin signaling and angiogenesis maintain endothelial cell health, it is plausible that women with pre-existing insulin resistance have an exaggerated response to alterations in angiogenic factors, and alterations in both pathways act synergistically to magnify the risk for PE. The present invention provides epidemiological evidence that an interaction exists between insulin resistance and angiogenesis.

The invention provides methods for utilizing an insulin resistance biomarker, such as SHBG, and an angiogenic biomarker, such as PlGF, as indicators of the risk for developing various pregnancy complications. SHBG and PlGF levels can be used in conjunction with other biomarker levels, such as a cytokine or growth factor, to predict the likelihood of a subject developing a gestational disorder. Importantly, unlike other markers of insulin resistance, SHBG is reliable in the fasting or non-fasting state and exhibits minimal diurnal variation (Hamilton-Fairley et al., Clin, Endocrinol. (Oxford), 43:159 (1995)). These features render SHBG a unique marker of insulin resistance, especially useful in clinical situations when fasting blood samples are not routinely collected, such as during prenatal obstetric care.

Sex hormone binding globulin (SHBG) is a glycoprotein synthesized by the liver that binds circulating estrogens and testosterone. Hepatic SHBG production is inhibited by insulin and thus, a reduced SHBG level is a marker of hyperinsulinemia and insulin resistance. The clinical utility of SHBG measurement as an index of insulin resistance was established in studies in which a reduced SHBG level was associated with increased risk of future type II diabetes in otherwise healthy women (see, e.g., Lindstedt et al., Diabetes, 40:123 (1991) and Haffner et al., J. Clin. Endocrinol. Metab., 77:56 (1993)). In normal pregnancy, SHBG levels rise steadily during the first and second trimesters, reaching a peak that is 4-6 times the normal non-pregnant range.

During the first-trimester of pregnancy, SHBG levels increase 3 to 5-fold above the normal range in healthy menstruating women (Kerlan et al., Clin. Endocrinol. (Oxford), 40:253 (1994), O'Leary et al., Clin. Chem., 37:667 (1991)). This early gestation increase in SHBG level mirrors the contemporaneous increase in estradiol level, which rises almost 20-fold during the first-trimester alone (id.).

The estradiol level continues to rise through the end of pregnancy such that by delivery, the level reaches greater than 100 times the normal, non-pregnant, early follicular-phase range. In contrast, SHBG peaks at a level that is 4-6 times the normal non-pregnant range within 24 weeks of gestation, and thereafter the level remains constant through the duration of pregnancy. Insulin resistance and insulin levels also increase progressively during normal gestation, but the greatest increment occurs during the second half of pregnancy (see, e.g., Catalano et al., Am. J. Obstet. Gynecol., 165:1667 (1991), Stanley et al., Br. J. Obstet. Gynaecol., 105:756 (1998)). This physiologic increase in insulin resistance during the third-trimester may prevent further increases in SHBG levels that otherwise would be expected in the setting of progressive increases in estradiol levels.

The association identified herein between first-trimester SHBG and PlGF levels and adverse pregnancy outcome in the univariate and multivariable analyses indicate that insulin resistance contributes to the pathogenesis of preeclampsia, gestational hypertension, and gestational diabetes. Furthermore, it demonstrates that first-trimester SHBG measurements are a useful screening method for identifying women at high risk for these disorders.

Methods of Identifying At-risk Subjects

Insulin resistance and Metabolic Syndrome characterize women who develop preeclampsia (PE). Angiogenesis-related growth factors (PlGF) and their inhibitors (sFlt1) have been associated with developing PE. The present invention provides the first evidence that in PE the levels of maternal factors (e.g., insulin resistance) and the levels of placental factors (e.g., indicators of angiogenesis, such as PlGF and sFlt1) can be correlated (i.e., they are additive insults) to epidemiologically predict a pregnant women's risk for developing a gestational disorder such as preeclampsia. More specifically, alterations in two pathways, insulin resistance (e.g., as evidenced by abnormal SHBG or cytokine (such as IL-6) levels) and angiogenesis (e.g., as evidenced by low PlGF or high sFlt1), when combined can be used to predict gestational disorders.

Metabolic syndrome and insulin resistance (characterized by measures of insulin resistance including elevated insulin levels, altered glucose levels, a marker of this syndrome namely low levels of Sex Hormone Binding Globulin (SHBG), elevated lipid levels, elevated body mass index, elevated inflammatory markers, and altered clotting factors) interact epidemiologically and biologically with angiogenesis factors to confer increased risk of Preeclampsia and related diseases, including risk of cardiovascular disease and diabetes. SHBG adds a significant amount of explanatory information (predictive information) to PlGF and sFlt1, and the combination provides a mechanism for identifying at-risk subjects.

Because of the natural increase in SHBG levels during pregnancy, and given the other factors known to influence SHBG levels, for use in the new methods, the results of SHBG levels can be adjusted for the number of weeks into the pregnancy (i.e., gestational age at the time of the blood sampling). In addition, the levels of SHBG can also be adjusted for one or more of age, gestational age, grace, estradiol and testosterone levels, and body mass index (BMI).

Baseline characteristics of the study population are shown in Table 1 (in the Examples, below). Women who developed preeclampsia (PE) were more likely to be nulliparous, had a higher body mass index, and higher systolic blood pressure compared to normotensive controls. In addition, gestational ages at delivery were earlier and fetal birth weights were lower among women who developed PE compared to controls.

First prenatal visit blood collections revealed that serum levels of placental growth factor (PlGF) and sex hormone binding globulin (SHBG) were significantly lower among women who subsequently developed PE compared to normotensive controls (Table 2, in Examples). At this early stage of pregnancy, serum levels of sFlt1 did not markedly differ between the two groups, but the trend suggested that women who developed PE had elevated levels even at this early stage of pregnancy. The correlation between PlGF and SHBG was strongly positive (r=0.58, P<0.001), suggesting that women with low baseline levels of PlGF also had low levels of serum SHBG. The correlation between sFlt1 and SHBG was r=0.17, P=0.10.

Serum levels of PlGF were then divided into a binomial variable (low vs. high) with cutpoints based on the $25^{th}$ percentile of the control population ($\leq$20 pg/ml vs. >20 pg/ml). In the unadjusted analysis, women with low baseline serum PlGF levels had a 6-fold increased risk of developing preeclampsia compared to women with high baseline PlGF levels (Table 3, in the Examples). After adjusting for maternal age, gestational age of blood collection, race, parity, body mass index, systolic blood pressure, and serum levels of sFlt-1 and SHBG, the point estimate increased slightly (Table 3). Importantly, the model fit (area under the curve) improved when SHBG was added to the model (0.80 to 0.86), suggesting the inclusion of SHBG in the analyses did not represent an over-adjustment of the model, but an improvement.

Next, stratum specific point estimates were examined based on low ($\leq$175 mg/dl) and high (>175 mg/dl) levels of SHBG (again representing the $25^{th}$ percentile among controls). These analyses revealed markedly different point estimates for PlGF between the two strata. In the strata of women with low serum levels of SHBG, the risk of preeclampsia among women with low serum levels of PlGF was 25.5, whereas the estimate among women with high levels of SHBG (and low levels of PlGF) was 1.8 (Table 3). Thus, differences in these observed point estimates in stratified analyses suggested that the effect of PlGF was modified by different degrees of insulin resistance. The suggestion of an interaction or effect modification was explored further.

In a univariate model, the interaction term PlGF×SHBG was statistically significant (Wald p=0.02). However, in the adjusted model (including other confounders, serum PlGF, sFlt1, and SHBG), the interaction term was no longer significant (Wald p=0.10) and the confidence intervals expectedly widened. We then included interaction terms based on the previously examined cutpoints into a multivariable model adjusting for important confounders. In this model with three (n-1) interaction terms (high PlGF and high SHBG, and reference), the risk of developing preeclampsia among women with low first trimester levels of PlGF and SHBG was approximately twice the risk found among women with low PlGF levels alone, and four times the risk among women with low SHBG levels alone (Table 3). Importantly, these estimates did not markedly differ when these analyses were restricted to nulliparous (low PlGF and low SHBG, OR 13.8, 95% CI 1.5-124.2) or multiparous (OR, 15.7, 95% CI 0.9-276.6) women, suggesting baseline differences in parity did not explain our findings (other data not shown).

The 3-D graph shown in FIG. 1 indicates that the pregnant subjects with SHBG levels that are lower than a reference subject (i.e., < about 175 nmol/L) and PlGF levels that are lower than a reference subject (i.e., < about 20 pg/ml/L) are at increased risk of developing a gestational disorder. The graph also indicates that there are at least four risk categories: very low risk, low risk, intermediate risk, and high risk. Specifically, a low SHBG level and low PlGF level corresponds to high risk. A high SHGB level and high PlGF level corresponds to very low risk. A low SHGB level and high PlGF level corresponds to low risk. A high SHGB level and low PlGF level corresponds to intermediate risk. Women who have results that indicate a low, intermediate, or high risk can then take steps to have additional tests done, and/or to be treated for a particular disorder. The new test is therefore useful not only to determine women at risk, but also to determine women who are not at risk for future gestational complications. Thus, the new test method can significantly reduce unnecessary testing later during the pregnancy.

These data provide the first evidence that women with alterations in markers for circulating angiogenic factors and in markers for insulin resistance were at increased risk for developing preeclampsia (PE) compared to women with alterations in either measure alone, and compared to women with neither alteration. Specifically, women with low levels of serum placental growth factor (PlGF) in the first trimester were at increased risk for developing subsequent PE, and this risk was exaggerated in women who also had low levels of SHBG, a surrogate marker of insulin resistance. The data indicate that there is a significant interaction between serum PlGF and SHBG such that the association between PlGF levels and the subsequent risk for PE was modified depending on the serum level of SHBG.

This finding of a compelling statistical interaction further indicates that critical molecular interactions between intracellular insulin signaling and angiogenesis occur. For example, binding of insulin to the insulin receptor leads to the activation of a variety of signaling pathways involving specific protein kinases, most important of which includes protein kinase B alpha/Akt kinase. This critical step governs cellular functions including apoptosis, metabolism, and proliferation. In addition, insulin also regulates the expression of genes involved in angiogenesis, including the expression of vascular endothelial growth factor (VEGF) mRNA, and VEGF (and likely PlGF) signaling also activates Akt phosphorylation. Interestingly, diabetic rats demonstrate a reduced cellular expression of VEGF mRNA, a process that may be rescued by insulin. Therefore, defects in the insulin receptor or in downstream insulin signaling pathways can lead to alterations in angiogenic factors. A combination of these insults can act synergistically to alter critical cellular functions, injure endothelial cells, and subsequently increase the risk for developing PE.

Normal angiogenesis is also a critical component of placental development. In addition to maintaining the integrity of endothelial cells, VEGF and PlGF are responsible for trophoblast proliferation, migration, and invasion, key processes that dictate normal placentation and which are altered in preeclampsia. Therefore, alterations in VEGF, PlGF, and their inhibitor sFlt1 can play pivotal roles in the pathogenesis of PE. In addition, however, insulin and insulin like growth factor play important roles in vascular function, including endothelial cell proliferation. Furthermore, investigators have identified alterations in insulin and insulin like growth factors at the level of the placenta in women with preeclampsia. Therefore, alterations in insulin or insulin like growth factors in the presence of alterations in VEFG, PlGF, and sFlt1 can act synergistically at the level of the placenta to lead to abnormal trophoblast invasion, explaining the placental findings characteristic of PE.

Specific alterations in inflammatory and insulin resistance cytokines (TNF-α, IL-1β, IL-6, MCP-1, and IL-8), angiogenesis related growth factors (PlGF, FGF-2), a growth factor antagonist (sFlt-1), and a biomarker for metabolic syndrome associated insulin resistance (i.e., sex hormone binding globulin (SHBG)) can be biologically linked to gestational disorders such as GDM and PIH. As discussed in further detail below, the invention is based, in part, on the discovery that a change in SHBG/PlGF levels, or antagonist thereof, in urine and/or blood prior to the third trimester of pregnancy, and as early as the first trimester, can be indicative of increased risk of preeclampsia, gestational hypertension, and gestational diabetes. Methods of determining whether a pregnant subject has, or is predisposed to having, a gestational disorder, are provided.

In one embodiment, the invention provides methods of determining whether a pregnant subject has, or is predisposed to having, a gestational disorder including measuring the level of sex hormone binding globulin (SHBG) in a serum sample obtained from the pregnant subject; measuring the level of placental growth factor (PlGF) in a serum sample or a urine sample obtained from the pregnant subject; comparing the SHBG level obtained from the pregnant subject with an SHBG level obtained from at least one subject having a normal pregnancy; and comparing the PlGF level obtained from the pregnant subject with a PlGF level obtained from at least one subject having a normal pregnancy. A low level of SHBG and/or PlGF present in the sample obtained from the pregnant subject, as compared to the levels present in the at least one subject having a normal pregnancy, indicates that the pregnant subject has, or is predisposed to having, a gestational disorder. SHBG and/or PlGF levels are correlated with: 1) the gestational age at the time SHBG and PlGF levels are measured; 2) the pregnant subject's age; 3) the pregnant subject's parity; and 4) the pregnant subject's body mass index. As used herein, a "low level" of SHBG or PlGF can be defined as a level that is less than the level of SHBG or PlGF detected in a subject having a normal pregnancy. In general, the levels of SHBG and PlGF are comparable between a test subject and a subject having a normal pregnancy when the samples are taken from both subjects at about at week "x" within the subject pregnancy plus or minus 1-2 weeks (see below). Alternatively, the level of SHBG or PlGF can be defined as "low" in comparison to a threshold value established by one or multiple reference subjects. Exemplary threshold values 175 nmol/L and 20 pg/ml for SHBG and PlGF, respectively, are provided in FIG. 1 as discussed herein.

The methods can further include measuring the level of at least one cytokine in the subject urine sample and generating a subject profile comprising a value or plurality of values, each value representing a level of a specific cytokine and comparing the subject profile with a reference profile, wherein the reference profile includes a value or plurality of values, each value representing a level of a specific cytokine in a reference urine sample obtained from a reference subject. References levels of cytokines and/or growth factors can be used to generate reference profiles. For example, the reference profile can be obtained from the urine, serum, plasma, amniotic fluid or placental tissue of a reference subject. A reference subject can be a pregnant individual having a gestational disorder and pregnant individual having a normal pregnancy.

A "gestational disorder" as used herein includes pregnancy-induced hypertension (PIH), such as preeclampsia (PE) or gestational hypertension (GH). A gestational disorder further includes gestational diabetes mellitus (GDM). A "normal" pregnancy, as used herein, is a pregnancy that is not associated with a gestational disorder.

A "subject" profile is generally described as a "test" profile. A subject profile can be generated from a sample taken from a subject prior to the third trimester to identify the subject's risk of developing GDM and/or PIH. Thus, a "subject" profile is generated from a subject being tested for a gestational disorder.

A "reference" profile is generally a "control" profile. A reference profile can be generated from a sample taken at a particular time point in the pregnancy of a normal individual or one having a gestational disorder. The reference profile, or plurality of reference profiles, can be used to establish threshold values for the levels of, for example, specific cytokines in a sample or SHGB and PlGF levels in a sample. A "reference" profile can be either a profile generated from an individual pregnant woman having a gestational disorder or a profile generated from a pregnant woman having a normal pregnancy. Alternatively, a reference profile can be a profile generated from either set of pregnant women having a gestational disorder or a set of pregnant women having normal pregnancies. A reference profile can be expressed as an array "signature" or "pattern" of specific identifiable biomarkers. The array signature can be color-coded for easy visual or computer-aided identification. The signature can also be described as one or more numbers that correspond to values attributed to the biomarkers identified by the array. The key shown in FIG. 2 (right side) provides one example of how values can be attributed to biomarker concentrations identified by an array. "Array analysis," as used herein, is the process of extrapolating information from an array using statistical calculations such as factor analysis or principle component analysis (PCA).

In addition to being expressed as a signature, a reference profile can be expressed as a "threshold" value or series of threshold values. For example, a single threshold value can be determined for the level of SHGB or PlGF in a pregnant subject. Exemplary threshold values for SHGB (about 175 nmol/L) and PlGF (about 20 pg/ml) are provided in Table 3 and FIG. 1. With regard to cytokine levels, a single threshold value can be determined by averaging the values of a series of cytokine levels from pregnant women having normal pregnancies. Similarly, a single or two or more threshold values can be determined by averaging the values of a series of cytokine levels from pregnant women having a gestational disorder. Thus, a threshold value can have a single value or a plurality of values, each value representing a level of a specific cytokine or growth factor, or antagonist thereof, detected in a urine or blood sample, e.g., of a pregnant individual, or multiple individuals, having a gestational disorder.

Figure 2:
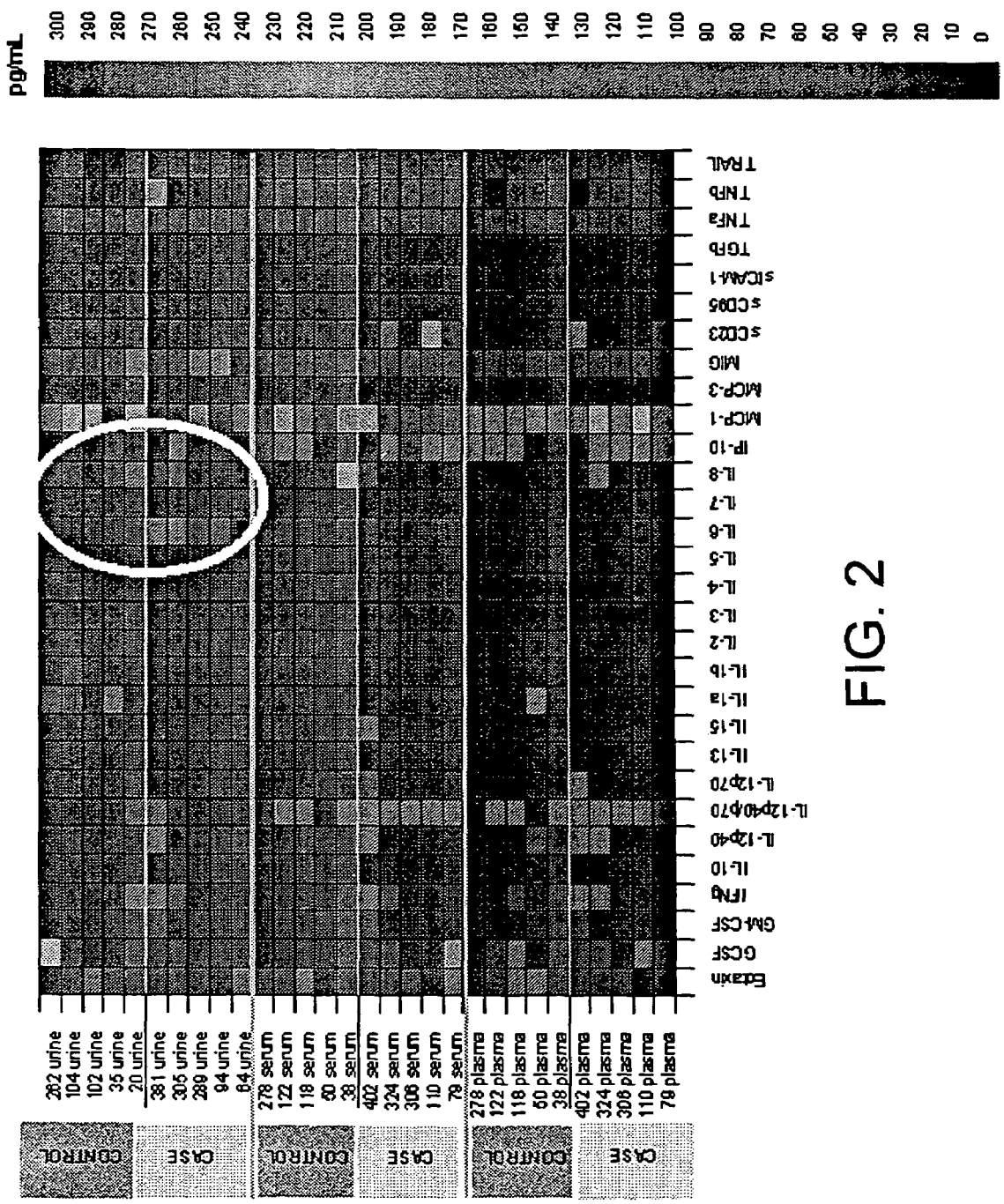
FIG. 2 is a heat map of a cytokine array that depicts the correlation between cytokine levels in urine and the risk of developing a gestational disorder.

For example, when also considering cytokine values, FIG. 2 shows that a threshold value for MCP-1 levels derived from samples obtained from pregnant women having normal pregnancies can be calculated based on the average of all 5 urine samples (see "control" horizontal columns for patients designated 262, 104, 102, 35, and 20 and corresponding vertical MCP-1 column). The average level of MCP-1 (assuming 90+230+210+300+210 pg/mL) is approximately 200 pg/mL. A comparison of these data to the MCP-1 levels in urine samples from patients designated 381, 305, 289, 94, and 64 indicates that an MCP-1 level below about 200 pg/mL is indicative of a normal pregnancy. In contrast, a pregnant female having a level of MCP-1 in her urine that exceeds about 200 pg/mL at 16-18 weeks of gestation is predicted to be at risk for developing a gestational disorder. Similarly, urine samples taken from the same patients indicate that an IL-6 level above about 20 pg/mL is indicative of a gestational disorder. Further, urine samples taken from the same patients indicate that an IL-8 level below about 200 pg/mL is indicative of a gestational disorder.

The samples used to generate a profile of the invention, including levels of SHBG and PlGF can be obtained at between about 6 and 24 weeks, between about 12 and 24 weeks, or between about 18 and 24 weeks after conception. Typically, the sample is taken prior to the third trimester, e.g., at any time between 5 to 24 weeks after conception (e.g., 8, 10, 12, 14, 16, 18, or 20 weeks). For example, a biological sample can be obtained from a pregnant female at between about 6 and 24 weeks, between about 12 and 24 weeks, or between about 18 and 24 weeks after conception. The sample can be used to generate a subject profile or a reference profile.

A subject profile or reference profile is generated from a sample taken at a time point in the pregnancy. The sample can be blood, serum or urine. The subject and reference profiles are generated from samples taken from similar time periods within the subject and reference pregnancies. In general, if a subject profile is generated from a sample taken at week "x" within the subject pregnancy, then the appropriate reference profile for comparison purposes will have been generated from a sample taken at week "x" plus or minus 2 weeks (or 1 week) of the reference pregnancy. For example, a subject profile derived from a sample obtained from a pregnant female estimated to be in her 16th week of pregnancy can be compared with a reference profile, or a plurality of reference profiles, derived from samples obtained from pregnant females in their 14th to 18th week of pregnancy.

Women having, or predisposed to having, a gestational disorder can be identified prior to the third trimester of pregnancy. A biomarker can be a cytokine, a growth factor, or a growth factor inhibitor. More specifically, an insulin resistance biomarker or angiogenic biomarker includes cytokines, growth factors, and growth factor inhibitors. An insulin resistance biomarker includes SHBG. An angiogenic biomarker includes PlGF.

A subject profile can include the level SHBG and PlGF in a blood, surface serum or urine sample obtained from a pregnant subject. The profile can further include the level of at least two cytokines detected in a urine sample from a subject and comparing the subject profile to a "reference" profile that includes the level of SHBG and PlGF obtained from a normal pregnant subject. The reference profile can further include the level of at least two cytokines detected in a urine sample. If the reference profile is derived from a sample obtained from a reference subject having a normal pregnancy, then the similarity of the subject profile to the reference profile is indicative of a normal (non-gestational disorder-associated) pregnancy for the tested subject. Alternatively, if the reference profile is derived from a sample obtained from a reference subject having a gestational disorder, then the similarity of the subject profile to the reference profile is indicative of a gestational disorder-associated pregnancy for the tested subject.

Cytokines

The methods of the invention can further include correlating SHBG and PlGF levels with levels of one or more cytokines, in blood and/or serum samples. The cytokine can be an immune/hematopoietin, an interferon, a tumor necrosis factor (TNF)-related molecule or a chemokine. Examples include interleukin (IL)-6, IL-8, IL-1β, monocyte chemoattractant protein (MCP)-1 or TNF-α, or any combination thereof. Cytokines comprise a vast array of relatively low molecular weight, pharmacologically active proteins that are secreted by cells for the purpose of altering either their own functions (autocrine effect) or those of adjacent cells (paracrine effect). In many instances, individual cytokines have multiple biological activities. Different cytokines can also have the same activity, which provides for functional redundancy within the inflammatory and immune systems. As a result, it is infrequent that loss or neutralization of one cytokine will markedly interfere with either of these systems. This fact has great significance in the development of therapeutic strategies.

Cytokines can be subdivided into several groups, including the immune/hematopoietins, interferons, tumor necrosis factor (TNF)-related molecules, and the chemokines. Representative immune/hematopoietins include erythropoietin (EPO), granulocyte/macrophage colony-stimulating factor (GM-CSF), granulocyte colony-stimulating factor (G-CSF), leukemia inhibition factor (LIF), oncostatin-M (OSM), ciliary neurotrophic factor (CNTF), growth hormone (GH), prolactin (PRL), interleukin (IL)-2, IL-3, IL-4, IL-5, IL-6, IL-7, IL-9, IL-10, and IL-12. Representative interferons (IFN) include IFNα IFNβ, and IFN-gamma.

Representative TNF family members include TNFα, interferon (IFN)β, gp$^{39}$ (CD40-L), CD27-L, CD30-L, and nerve growth factor (NGF).

Representative chemokines include platelet factor (PF)4, platelet basic protein (PBP), groα, MIG, ENA-78, macrophage inflammatory protein (MIP)1α, MIP1β, monocyte chemoattractant protein (MCP)-1, I-309, HC14, C10, Regulated on Activation, Normal T-cell Expressed, and Secreted (RANTES), and IL-8.

Chemokines are a family of structurally related glycoproteins with potent leukocyte activation and/or chemotactic activity. They are 70 to 90 amino acids in length and approximately 8 to 10 kDa in molecular weight. Most of them fit into two subfamilies with four cysteine residues. These subfamilies are distinguished by whether the two amino terminal cysteine residues are immediately adjacent to each other or separated by one amino acid. The chemokines, also known as CXC chemokines, contain a single amino acid between the first and second cysteine residues; β, or CC, chemokines have adjacent cysteine residues. Most CXC chemokines are chemoattractants for neutrophils whereas CC chemokines generally attract monocytes, lymphocytes, basophils, and eosinophils. There are also 2 other small sub-groups. The C group has one member (lymphotactin). It lacks one of the cysteines in the four-cysteine motif, but shares homology at its carboxyl terminus with the C—C chemokines. The C chemokine seems to be lymphocyte specific. The fourth subgroup is the C-X3-C subgroup. The C-X3-C chemokine (fractalkine/neurotactin) have three amino acid residues between the first two cysteines. They are tethered directly to the cell membrane via a long mucin stalk and induce both adhesion and migration of leukocytes.

The heat map of the cytokine array in urine, serum, and plasma shown in FIG. 2 demonstrates that among women who developed preeclampsia ("cases"), IL-6 is elevated and IL-8 is reduced (see white circle) in the urine at 16-18 weeks of gestation compared to women who had a normotensive pregnancy and with urine samples collected at the same time. This is the first time an array of cytokines was measured in urine by this sensitive technique and the first time differences were seen in urine at this early stage of pregnancy. FIG. 2 also demonstrates that at 16 weeks of gestation the levels of another chemokine, MCP-1, were elevated in the urine of cases as compared to controls. All protein measurements were normalized for urine creatinine concentrations.

Growth Factors

The method further includes measuring the level of at least one growth factor inhibitor, such as placental soluble fms-like tyrosine kinase 1 (sFlt1), or a growth factor such as VEGF. SFlt1, a splice variant of the VEGF receptor lacking the transmembrane and cytoplasmic domains, acts as a potent VEGF and PlGF antagonist. Sflt1 is known to be upregulated in preeclampsia, leading to increased systemic levels of sFlt1 that fall after delivery (Maynard et al., J. Clinical Invest., 111:5, 2003, incorporated herein by reference). Increased circulating sFlt1 in patients with preeclampsia is associated with decreased circulating levels of free VEGF and PlGF.

Placental growth factor (PlGF), a member of the vascular endothelial growth factor (VEGF) family of angiogenic factors (58% sequence identity to VEGF), and other placental VEGF's can contribute to the pathogenesis of GDM and PIH. Furthermore, cytokines and growth factors appear to cooperate in the progression of certain pathological disorders. For example, IL-6 is known to promote cervical and pancreatic cancer and multiple myeloma activity. These processes are also mediated by VEGF (Wei et al., Oncogene, 22:1517, 2003.). In addition, TNF-α is involved in VEGF secretion by myeloma cells (Alexandrakis et al., Ann Hematol, 82:19, 2003). Growth factors and cytokines can act on the same target cells, as VEGF and IL-8 both activate monocytes and endothelial cell proliferation, and IL-8 itself can be involved in angiogenesis. Growth factors and cytokines may regulate each other, as PlGF not only activates monocytes, it also increases transcription of inflammatory cytokines (TNF-α, IL-1β) and chemokines (MCP-1, IL-8). Finally, growth factors may counterbalance cytokine-mediated injury, as TNF-α induces apoptosis of trophoblast cells, and placental growth factors, such as fibroblast growth factor-2 (FGF-2), mitigate this process (Garcia-Lloret et al., J Cell Physiol, 167:324, 1996). The function of cytokines and growth factors are likely intertwined, in that normal function of both are necessary for normal placental development, and hence alterations in both may lead to a gestational disorder. Simultaneous examination of both can provide a more accurate method for identifying whether a subject has, or is predisposed to having, a gestational disorder.

The invention also encompasses the use of a combination of cytokine and growth factor level alterations as indicators of future disease. For example, one case subject had a urinary PlGF level of 91.2 pg/gCr (high, not consistent with PE), but had an IL-6 level of 58 pg/gCr (high, consistent with PE), and an MCP-1 level of 460 pg/gCr (high, consistent with PE). Thus, a single urine measurement of PlGF would have incorrectly suggested this woman was not at risk for PE, but examination of IL-6 and MCP-1 levels would have suggested just the opposite. Another example, a control subject, PlGF level was 115.2 pg/gCr (high, consistent with low risk of PE) and IL-6 levels were 20 pg/gCr (low, consistent with low risk for PE), but MCP-1 level was 410 pg/gCr (high, consistent with high risk for PE), therefore, utilizing only MCP-1 levels would have incorrectly predicted her outcome. Therefore, the invention also encompasses the use of patterns of levels of cytokines and growth factors in serum and/or urine to determine a subject's predisposition to a future disease associated with pregnancy-induced hypertension.

In another embodiment, the invention provides a method of identifying a gestational disorder by comparing the level of TNF-α, IL-1β, IL-6, IL-8 or MCP-1, or any combination thereof, in a first biological sample from a pregnant subject the cytokine level in a second biological sample obtained from the same pregnant subject. A difference in the level of a cytokine, or any combination of cytokines, in the first sample as compared to the second sample is indicative of a subject having, or predisposed to having, a gestational disorder. The first and second biological samples can be selected from urine, blood, serum, amniotic fluid, or placental tissue.

An exemplary biochemical test for identifying specific proteins, such as cytokines, growth factors, or antagonists thereof, employs a standardized test format, such as the Enzyme Linked Immunosorbent Assay or ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests).

It is understood that commercial assay enzyme-linked immunosorbant assay (ELISA) kits for various cytokines and growth factors are available. For example, with regard to growth factors, sFlt-1, PlGF, and FGF-2 ELISA kits are available from R&D systems. These kits can measure free or unbound proteins. The intra-assay precision CV (%) for sFlt-1 and PlGF are about 3.5 and 5.6 respectively. The inter-assay precision CV(%) for sFlt-1 and PlGF are about 8.1 and 10.9 respectively. For serum FGF-2 measurements, the intra-assay and inter-assay CV(%) are about 8 and 12.7 respectively. For urine PlGF and FGF-2, the intra-assay and inter-assay CV(%) are about 11, 9.8, 12.1 and 14.4, respectively.

Proteomics and Microarrays

The invention provides methods for predicting adverse outcomes of pregnancy well before the end of pregnancy through the use of proteomics. Proteomics is an evolving technology capable of testing for the presence of minute amounts of a vast array of proteins using small samples of human tissue. Using proteomic tools, increased or decreased levels of certain proteins in a biological sample such as urine, serum, amniotic fluid, or placental tissue can be ascertained. The invention encompasses urine proteomic analysis as a non-invasive approach to diagnosing pregnancy complications remote from term. In addition, using mathematical algorithms a complex proteome or "fingerprint" can be obtained. As previously noted, such algorithms include "factor analyses" and "principle component analysis (PCA)." The proteome can consist of a group of proteins, some increased in concentration from normal and others decreased, that are diagnostic of gestational disorders, such as those associated with PIH and/or GDM.

The invention provides an array (i.e., "biochip" or "microarray") that includes immobilized biomolecules that facilitate the detection of a particular molecule or molecules in a biological sample. Biomolecules that identify the biomarkers described above and shown in FIG. 2 can be included in a custom array for detecting subjects predisposed to GDM and/or PIH. For example, a custom array can include biomolecules that identify SHBG and/or PlGF, or specific cytokines such as IL-6, IL-8, and MCP-1. The array can also include biomolecules that identify additional growth factors such as FGF-2. The array can further include a biomolecule that identifies a growth factor antagonist, such as sFlt-1. Arrays comprising biomolecules that specifically identify selected biomarkers (e.g., a cytokine or a growth factor or antagonist thereof) can be used to develop a database of information using data provided in the present specification. Additional biomolecules that identify cytokines and/or growth factors which lead to improved cross-validated error rates in multivariate prediction models (e.g., logistic regression, discriminant analysis, or regression tree models) can be included in a custom array of the invention.

Customized array(s) provide an opportunity to study the biology of GDM and PIH. Standard p values of significance (0.05) can be chosen to exclude or include additional specific biomolecules on the microarray that identify particular biomarkers.

The term "array," as used herein, generally refers to a predetermined spatial arrangement of binding islands, biomolecules, or spatial arrangements of binding islands or biomolecules. Arrays according to the present invention that include biomolecules immobilized on a surface may also be referred to as "biomolecule arrays." Arrays according to the present invention that comprise surfaces activated, adapted, prepared, or modified to facilitate the binding of biomolecules to the surface may also be referred to as "binding arrays." Further, the term "array" may be used herein to refer to multiple arrays arranged on a surface, such as would be the case where a surface bore multiple copies of an array. Such surfaces bearing multiple arrays may also be referred to as "multiple arrays" or "repeating arrays." The use of the term "array" herein may encompass biomolecule arrays, binding arrays, multiple arrays, and any combination thereof; the appropriate meaning will be apparent from context. An array can include cytokine-specific biomolecules that detect cytokines and other proteins altered in a gestational disorder. The biological sample can include fluid or solid samples from any tissue of the body including excretory fluids such as urine. Non-urine samples include, but are not limited to serum, plasma, amniotic fluid, and placental tissue.

An array of the invention comprises a substrate. By "substrate" or "solid support" or other grammatical equivalents, herein is meant any material appropriate for the attachment of biomolecules and is amenable to at least one detection method. As will be appreciated by those in the art, the number of possible substrates is very large. Possible substrates include, but are not limited to, glass and modified or functionalized glass, plastics (including acrylics, polystyrene and copolymers of styrene and other materials, polypropylene, polyethylene, polybutylene, polyurethanes, TEFLON®, etc.), polysaccharides, nylon or nitrocellulose, resins, silica or silica-based materials including silicon and modified silicon, carbon, metals, inorganic glasses, plastics, ceramics, and a variety of other polymers. In addition, as is known the art, the substrate may be coated with any number of materials, including polymers, such as dextrans, acrylamides, gelatins or agarose. Such coatings can facilitate the use of the array with a biological sample derived from urine or serum.

A planar array of the invention will generally contain addressable locations (e.g., "pads", "addresses," or "microlocations") of biomolecules in an array format. The size of the array will depend on the composition and end use of the array. Arrays containing from about 2 different biomolecules to many thousands can be made. Generally, the array will comprise from two to as many as 100,000 or more, depending on the end use of the array. A microarray of the invention will generally comprise at least one biomolecule that identifies or "captures" a biomarker, such as SHBG, PlGF, a cytokine, growth factor, or antagonist thereof, present in a biological sample. In some embodiments, the compositions of the invention may not be in an array format; that is, for some embodiments, compositions comprising a single biomolecule may be made as well. In addition, in some arrays, multiple substrates may be used, either of different or identical compositions. Thus, for example, large planar arrays may comprise a plurality of smaller substrates.

As an alternative to planar arrays, bead based assays in combination with flow cytometry have been developed to perform multiparametric immunoassays. In bead based assay systems the biomolecules can be immobilized on addressable microspheres. Each biomolecule for each individual immunoassay is coupled to a distinct type of microsphere (i.e., "microbead") and the immunoassay reaction takes place on the surface of the microspheres. Dyed microspheres with discrete fluorescence intensities are loaded separately with their appropriate biomolecules. The different bead sets carrying different capture probes can be pooled as necessary to generate custom bead arrays. Bead arrays are then incubated with the sample in a single reaction vessel to perform the immunoassay.

Product formation of the biomarker with their immobilized capture biomolecules can be detected with a fluorescence based reporter system. Biomarkers, such as cytokines, growth factors or antagonists thereof, can either be labeled directly by a fluorogen or detected by a second fluorescently labeled capture biomolecule. The signal intensities derived from captured biomarkers are measured in a flow cytometer. The flow cytometer first identifies each microsphere by its individual color code. Second the amount of captured biomarkers on each individual bead is measured by the second color fluorescence specific for the bound target. This allows multiplexed quantitation of multiple targets from a single sample within the same experiment. Sensitivity, reliability and accuracy are compared to standard microtiter ELISA procedures. With bead based immunoassay systems cytokines can be simultaneously quantified from biological samples. An advantage of bead-based systems is the individual coupling of the capture biomolecule to distinct microspheres.

Thus, microbead array technology can be used to sort cytokines, growth factor or growth factor antagonists, bound to a specific biomolecule using a plurality of microbeads, each of which can carry about 100,000 identical molecules of a specific anti-tag biomolecule on the surface of a microbead. Once captured, the biomarker, such as a cytokine, can be handled as fluid, referred to herein as a "fluid microarray."

An array of the present invention encompasses any means for detecting a biomarker molecule such as a cytokine, growth factor, or antagonist thereof. For example, microarrays can be biochips that provide high-density immobilized arrays of recognition molecules (e.g., antibodies), where biomarker binding is monitored indirectly (e.g., via fluorescence). In addition, an array can be of a format that involves the capture of proteins by biochemical or intermolecular interaction, coupled with direct detection by mass spectrometry (MS).

Arrays and microarrays that can be used with the new methods to detect the biomarkers described herein can be made according to the methods described in U.S. Pat. Nos. 6,329,209; 6,365,418; 6,406,921; 6,475,808; and 6,475,809, and U.S. patent application Ser. No. 10/884,269, which are incorporated herein in their entirety. For example, the Zyomyx Human Cytokine Biochip® provides a highly sensitive protein profiling system for 30 biologically relevant cytokines. New arrays, to detect specific selections of sets of biomarkers described herein can also be made using the methods described in these patents.

Arrays and microarrays as used herein further include arrays that have pathogen-encoded cytokine-binding proteins immobilized on a solid surface. For example, poxvirus genes encoding binding activities for TNF type I and type II interferons, interleukin (IL)-1beta, IL-18, and beta-chemokines have been identified. These high-affinity receptors have the potential to act as surrogate antibodies in a number of applications in cytokine quantification and purification and could be potentially useful reagents to complement the existing panel of anti-cytokine, monoclonal, polyclonal, or engineered antibodies that are currently available.

In many embodiments, immobilized biomolecules, or biomolecules to be immobilized, are proteins. One or more types of proteins may be immobilized on a surface. In certain embodiments, the proteins are immobilized using methods and materials that minimize the denaturing of the proteins, that minimize alterations in the activity of the proteins, or that minimize interactions between the protein and the surface on which they are immobilized.

Surfaces useful according to the present invention may be of any desired shape (form) and size. Non-limiting examples of surfaces include chips, continuous surfaces, curved surfaces, flexible surfaces, films, plates, sheets, tubes, and the like. Surfaces preferably have areas ranging from approximately a square micron to approximately 500 $cm^2$. The area, length, and width of surfaces according to the present invention may be varied according to the requirements of the assay to be performed. Considerations may include, for example, ease of handling, limitations of the material(s) of which the surface is formed, requirements of detection systems, requirements of deposition systems (e.g., arrayers), and the like.

In certain embodiments, it is desirable to employ a physical means for separating groups or arrays of binding islands or immobilized biomolecules: such physical separation facilitates exposure of different groups or arrays to different solutions of interest. Therefore, in certain embodiments, arrays are situated within wells of 96, 384, 1536, or 3456 microwell plates. In such embodiments, the bottoms of the wells may serve as surfaces for the formation of arrays, or arrays may be formed on other surfaces and then placed into wells. In certain embodiments, such as where a surface without wells is used, binding islands may be formed or biomolecules may be immobilized on a surface and a gasket having holes spatially arranged so that they correspond to the islands or biomolecules may be placed on the surface. Such a gasket is preferably liquid tight. A gasket may be placed on a surface at any time during the process of making the array and may be removed if separation of groups or arrays is no longer necessary.

The immobilized biomolecules can bind to molecules present in a biological sample overlying the immobilized biomolecules. Alternatively, the immobilized biomolecules modify or are modified by molecules present in a biological sample overlying the immobilized biomolecules. For example, a cytokine present in a biological sample can contact an immobilized biomolecule and bind to it, thereby facilitating detection of the cytokine. Alternatively, the cytokine or growth factor or antagonist thereof, can contact a biomolecule immobilized on a solid surface in a transient fashion and initiate a reaction that results in the detection of the cytokine absent the stable binding of the cytokine to the biomolecule.

Modifications or binding of biomolecules in solution or immobilized on an array may be detected using detection techniques known in the art. Examples of such techniques include immunological techniques such as competitive binding assays and sandwich assays; fluorescence detection using instruments such as confocal scanners, confocal microscopes, or CCD-based systems and techniques such as fluorescence, fluorescence polarization (FP), fluorescence resonant energy transfer (FRET), total internal reflection fluorescence (TIRF), fluorescence correlation spectroscopy (FCS); colorimetric/spectrometric techniques; surface plasmon resonance, by which changes in mass of materials adsorbed at surfaces may be measured; techniques using radioisotopes, including conventional radioisotope binding and scintillation proximity assays so (SPA); mass spectroscopy, such as matrix-assisted laser desorption/ionization mass spectroscopy (MALDI) and MALDI-time of flight (TOF) mass spectroscopy; ellipsometry, which is an optical method of measuring thickness of protein films; quartz crystal microbalance (QCM), a very sensitive method for measuring mass of materials adsorbing to surfaces; scanning probe microscopies, such as AFM and SEM; and techniques such as electrochemical, impedance, acoustic, microwave, and IR/Raman detection. See, e.g., Mere L, et al., "Miniaturized FRET assays and microfluidics: key components for ultra-high-throughput screening," Drug Discovery Today 4(8):363-369 (1999), and references cited therein; Lakowicz J R, Principles of Fluorescence Spectroscopy, 2nd Edition, Plenum Press (1999).

Arrays of the invention suitable for identifying a gestational disorder may be included in kits. Such kits may also include, as non-limiting examples, reagents useful for preparing biomolecules for immobilization onto binding islands or areas of an array, reagents useful for detecting modifications to immobilized biomolecules, or reagents useful for detecting binding of biomolecules from solutions of interest to immobilized biomolecules, and instructions for use.

Likewise, arrays comprising immobilized biomolecules may be included in kits. Such kits may also include, as non-limiting examples, reagents useful for detecting modifications to immobilized biomolecules or for detecting binding of biomolecules from solutions of interest to immobilized biomolecules.

Theranostics

The invention provides compositions and methods for the identification of women at high risk for adverse outcomes of pregnancy such that a theranostic approach can be taken to test such individuals to determine the effectiveness of a particular therapeutic intervention (pharmaceutical or non-pharmaceutical) and to alter the intervention to 1) reduce the risk of developing adverse outcomes and 2) enhance the effectiveness of the intervention. Thus, in addition to diagnosing or confirming the presence of or risk for a gestational disorder, the methods and compositions of the invention also provide a means of optimizing the treatment of a subject having such a disorder. The invention provides a theranostic approach to treating a gestational disorder by integrating diagnostics and therapeutics to improve the real-time treatment of a subject having, for example, GDH and/or PIH. Practically, this means creating tests that can identify which patients are most suited to a particular therapy, and providing feedback on how well a drug is working to optimize treatment regimens. In the area of diseases associated with pregnancy-induced hypertension, theranostics can flexibly monitor changes in important parameters (e.g., cytokine and/or growth factor levels) over time. For example, theranostic multiparameter immunoassays specific for a series of diagnostically relevant molecules such as SHBG and PlGF can be used to follow the progress of a subject undergoing treatment for PIH. The markers provided herein are particularly adaptable for use in diagnosis and treatment because they are available in easily obtained body fluids such as urine, blood or serum.

Within the clinical trial setting, a theranostic method or composition of the invention can provide key information to optimize trial design, monitor efficacy, and enhance drug safety. For instance, "trial design" theranostics can be used for patient stratification, determination of patient eligibility (inclusion/exclusion), creation of homogeneous treatment groups, and selection of patient samples that are representative of the general population. Such theranostic tests can therefore provide the means for patient efficacy enrichment, thereby minimizing the number of individuals needed for trial recruitment. "Efficacy" theranostics are useful for monitoring therapy and assessing efficacy criteria. Finally, "safety" theranostics can be used to prevent adverse drug reactions or avoid medication error.

Statistical Analyses

The data presented herein provides a database of information related to diagnosing gestational disorders. Classification and prediction provide a statistical approach to interpreting and utilizing the data generated by an array as shown in FIG. 2. Prediction rules can be selected based on cross-validation, and further validating the chosen rule on a separate cohort. A variety of approaches can be used to generate data predictive of a gestational disorder based on cytokine and/or growth factor levels provided herein, including discriminant analysis, logistic regression, and regression trees. For example, data can be generated based on logistic regression models. FIG. 9 illustrates a Bayesian discriminant analysis as applied to the data set of 5 proteins (cytokines) measured on each of 5 cases (subjects) and 5 controls (references) shown in FIG. 2. Discriminant analysis attempts to find a plane in the multivariate space of the marker data such that, to the extent possible, cases appear on one side of this plane, and controls on the other. The coefficients that determine this plane constitute a classification rule: a linear function of the marker values, which is compared with a threshold. In Bayesian classification, information on the probability of a subject being a case (i.e., a subject having, or predisposed to having, a gestational disorder) that is known before the data are obtained can be employed. For example the prior probability of being a case can be set to about 0.5; for a screening test applied to a general population the corresponding probability will be approximately 0.05. A subject is classified as having a complication (i.e., a gestational disorder) if the corresponding posterior probability (i.e., the prior probability updated using the data) exceeds 0.5. Note that 9 of 10 cases and controls are classified correctly (see FIG. 9).

Additional patient information can be combined with the SHBG and/or PlGF levels provided herein. These data can be combined in a database that analyzes the information to identify trends that complement the present biomarker data. Results can be stored in an electronic format.

The present methods use SHBG and PlGF levels, and optionally cytokine and/or additional growth factor levels, as biomarkers for determining the risk for developing various pregnancy complications related to gestational diabetes mellitus or PIH-related disorders, such as preeclampsia and gestational hypertension. Preeclampsia and gestational hypertension develop most commonly in nulliparous (first pregnancy) women who are obese and have high-normal blood pressure at baseline. These disorders also develop in women with a history of preexisting diabetes or gestational diabetes, and in women with polycystic ovary syndrome. In most cases, preeclampsia or gestational hypertension develops without warning, often in women without any of these established risk factors. Accordingly, the methods and compositions for identifying gestational disorder provided herein can be combined with the patient history to enhance the reliability of a medical diagnosis. The analysis can assess, for example, urine or serum biomarkers obtained from the patient through a sample. Further, information concerning the patient can be supplied in conjunction with the test. Such information includes, but is not limited to, age, weight (BMI), blood pressure, genetic history, parity, gestational age, and other such parameters or variables as described in the Examples below.

Confounders and covariates in the analysis of data generated to establish guidelines for GDM and PIH can be included in the database of information. These data can include, for example, age since aging is associated with an increase in circulating inflammatory cytokines. In addition, a correlation between ethnicity and cytokine genetic polymorphisms (IL-6, TNF-α, IL-10) can provide baseline levels of cytokines according to race. Smoking is an example of a confounder because it can lower sFlt-1 levels, increase VEGF levels, lower cytokine levels, increase risk for GDM, and a reduced risk of developing PE. Cytokine and growth factor alteration in women with a history of past and current smoking can be assessed and added to the database of information related to predicting GDM or PIH.

Obesity is a known risk factor for development of GDM and PE, and serum levels of specific cytokines, including TNF-α and IL-6, are both positively correlated with body mass index (BMI). BMI is calculated as the weight in kilograms divided by the square of the height in meters. In addition, growth factors including VEGF are secreted from adipocytes. Elevated BMI may be in the causal pathway, in that obesity leads to elevated cytokines, which leads to insulin resistance and inflammation, which then predisposes to GDM and PIH.

Fetal birth weight can be considered a secondary outcome as GDM and PE lead to increased and decreased fetal birth weights, respectively. This information will be included to determine the association between primary exposures and fetal birth weight in cases (i.e., those subjects exhibiting GDM and/or PIH) and controls. Preeclampsia is one cause of the heterogeneous disorder identified as fetal growth restriction (FGR). Growth factors from the placenta may be involved in the underlying pathophysiology of FGR, and, maternal serum and urine levels of specific growth factors and of may be altered in women with newborns who have FGR. For example, among women with PE, free PlGF levels at 15-19 weeks of gestation can be lower among women (n=18) who develop PE with small or gestational age newborns (birth weight <10th percentile), compared with women (n=25) who just developed PE. A random selection of nulliparous women can provide uncomplicated pregnancy-controls for comparison purposes. Such women can be, for example, normotensive throughout gestation; normoglycemic, full term (>37 weeks); no evidence of FGR; live birth; no elevated blood pressure or hyperglycemia at the 6 week postpartum visit.

The statistical analyses described above can be correlated with SHBG and PlGF levels as described herein. The primary outcomes will be GDM, PIH, and history of GDM, and PE. Descriptive statistics can be used to spot errors in coding (e.g., outliers), to determine if normality assumptions are met, if transformation is necessary (e.g., log cytokine levels) to improve normality, or if non-parametric approaches are needed. Covariate and confounder distributions can be examined (e.g., contingency tables).

In addition, the statistical analyses generated from the above information can be combined with information regarding cytokine and additional growth factor levels and growth factor antagonist levels described herein. Thus, the invention encompasses examining cytokine levels and growth factor levels (and their antagonists) in the same women and correlating this information to identify those individuals predisposed to GDM and/or PIH using additional statistical information such as BMI, blood pressure, and fetal birth weight.

Additional analyses can be performed to identify subjects at risk for GDM or PIH. Such analyses include bivariate analysis of each of the primary exposures, multivariate models including variables with a strong relationship (biologic and statistical) with outcomes, methods to account for multiple critical exposures including variable reduction using factor analysis, and prediction models.

For bivariate analysis, the mean level of each primary exposure between cases and controls using a 2-sample t-test or Wilcoxon Rank Sum test, as appropriate, can be conducted. If the association appears linear, trend can be analyzed using the Mantel Haenszel test. Data can be assembled into less fine categories (e.g., tertiles) using the distribution of the controls, and examine these as indicator variables in multivariable analysis.

For multivariate analyses, data can be correlated between two control groups, one matched and another not matched. In both matched and unmatched analyses, the independent effects of all primary exposures of interest can be examined using logistic regression (with conditional models in matched analyses) models. The models can include a minimum number of covariates to test the main effect of specific predictors. The effect of specific proteins can be determined in addition to pregnancy outcomes after accounting for confounders or potentially mediating variables. As noted above, Tables 1-5 are examples of such analyses.

Logistic regression models take the general form $[\ln(p_i/1-p_i)=b_0+b_1X1_i+b_2X2_i+ \ldots +b_nX_{ni}+e]$, where $p_i$ is the probability of GDM, $b_0$ represents the intercept of the fitted line, $b_1$ is the coefficient associated with a unit increase in the level of a growth factor such as SHBG, $b_2 \ldots b_n$ are the coefficients associated with confounding covariates $X2 \ldots Xn$, and e is an error term. The odds ratio associated with a unit increase in the level of a specific growth factor or cytokine is estimated by exponentiating the coefficient $b_1$, and the 95% confidence interval surrounding this point estimate is estimated by exponentiating the term $(b_1 \pm 1.96$ (standard error of $b_1$)). In models with more than one $b_n$ covariate, the effect of $b_1$ can be interpreted as the effect of the specific growth factor or cytokine level on risk of GDM and/or PIH after adjustment for levels of confounding covariates included in the model.

In factor analysis, specific cytokines can be reduced to a smaller number of inter-correlated cytokines. Factor scores derived from rotated principal components (which are normally distributed continuous variables) can be modeled instead of original cytokine levels in regression analyses predicting outcomes of pregnancy. This model-building strategy is similar to that described above, but modeling factor scores allowing the identification of specific cytokine signatures as predictive of outcomes independently of other cytokine signatures, or independently of BMI or other important pre-specified confounding or mediating variables.

The diverse array of potentially inter-correlated cytokines derived from array experiments can be reduced with factor analysis using principal component analysis. Principal component analysis identifies subsets of correlated variables that group together. These subsets define components: mathematically derived variables that are uncorrelated with each other and that explain the majority of the variance in the original data. Principal components analysis (PCA) attempts to identify a minimum number of components needed to make a diagnosis. After identification, components are transformed, or rotated, into interpretable factors. Interpretation is based on the pattern of correlations between the factors and the original independent variables; these correlations are called loadings. In array experiments, factor patterns represent domains or distinct groupings of cytokines underlying the overall relationships among the original array of putatively independent cytokine levels. These groupings may be considered as cytokine signature patterns.

Figure 8:
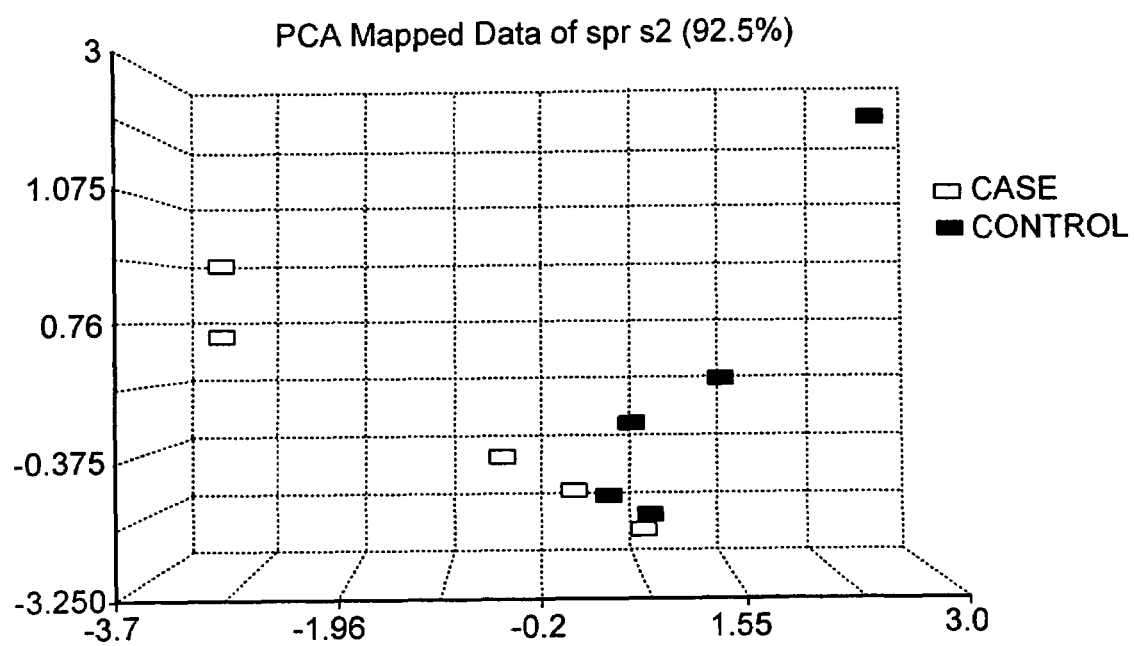
FIG. 8 depicts a three-dimensional graph of the results of a principal components analysis (PCA) of "case" (i.e., "subject) versus "control" (i.e., reference") growth factor data.

Using the patient data described in FIGS. 3 and 4, PCA analysis as shown in FIG. 8 was used to reduce the 5 explanatory cytokines (TNF-$\alpha$, IL-1$\beta$, IL-6, MCP-1, and IL-8) to 3 components, and showing that a separation is beginning to appear between cases (5 most left boxes) and controls (5 most right boxes). Factor analysis was performed using continuously distributed variables with the principal component option of the SAS FACTOR procedure. Variables may be transformed to improve normality, although principal components are fairly robust to normality deviations. Variables included in the factor analysis include all cytokine levels included in an array experiment, for example. In most cases the minimum number of components are selected based on components whose eigenvalues exceed unity. Eigenvalues are the sum of the squared correlations between the original independent variables and the principal components and represent the amounts of variance attributable to the components.

To avoid over-factored models one generally excludes components with eigenvalues equal to or barely exceeding unity that lie below the inflection point on a screen plot and that do not contribute additional clarity to the resultant factor pattern. To produce interpretable factors, the minimum number of principal components can be rotated using the orthogonal varimax method. This orthogonal rotation is a transformation of the original components that produces factors uncorrelated with each other (representing unique independent domains), but highly correlated with unique subsets of the original cytokines. In general, loadings (correlations between the factors and the original independent variables; range $-1.0$ to $1.0$) greater than $\pm 0.30$ are used to interpret the resulting factor pattern. Similarities between loadings on the same factor within selected subgroups (for example, Asian versus White women) can be evaluated using coefficients of congruence. The coefficient of congruence approaches unity when factor loadings are identical between subgroups.

Although factor analysis is not a strict hypothesis testing methodology, one can use Bartlett's method, which gives a value distributed approximately as chi-square, to test the null hypothesis that the first dominant factor may be significant, but remaining factors explain only error variance and are not significant. Confirmatory factor analyses can be conducted to assess whether an empirically determined model (e.g., a three factor solution with two independent variables loading on two factors) provides a better fit to the data than a model with all independent variables loading on a single factor (the null hypothesis model). Three goodness-of fit indices are generally employed: (i) the maximum likelihood goodness-of-fit index, which gives a value distributed as chi-square and where a smaller value indicates a better fit to the data, (ii) Bentler's non-normed fit, and (iii) Bentler and Bonett's comparative fit indices, where higher values (range, 0 to 1.0) indicate a better fit.

Databases and Computerized Methods of Analyzing Data

A database generated by the methods and analyses described herein can be included in, or associated with, a computer system for determining whether a pregnant subject has, or is predisposed to having, a gestational disorder. The database can include a plurality of digitally encoded "reference" (or "control") profiles. Each reference profile of the plurality can have a plurality of values, each value representing a level of SHBG or PlGF in a sample or a specific cytokine detected in blood, serum, or urine of a pregnant individual having, or predisposed to having, a gestational disorder. Alternatively, a reference profile can be derived from a pregnant individual who is normal. Both types of profiles can be included in the database for consecutive or simultaneous comparison to a subject profile. The computer system can include a server containing a computer-executable code for receiving a profile of a pregnant subject and identifying from the database a matching reference profile that is diagnostically relevant to the pregnant subject profile. The identified profile can be supplied to a caregiver for diagnosis or further analysis.

Using standard programs, electronic medical records (EMR) can be accumulated to provide a database that combines cytokine, growth factor, and growth factor antagonist data with additional information such as the BMI of a patient or any other parameter useful for predicting the risk of developing GDM or PIH. Patient information can be randomly assigned a numerical identifier to maintain anonymity with testing laboratories and for security purposes. All data can be stored on a network that provides access to multiple users from various geographic locations.

Thus, the various techniques, methods, and aspects of the invention described herein can be implemented in part or in whole using computer-based systems and methods. Additionally, computer-based systems and methods can be used to augment or enhance the functionality described herein, increase the speed at which the functions can be performed, and provide additional features and aspects as a part of, or in addition to, those of the invention described herein. Various computer-based systems, methods, and implementations in accordance with the above-described technology are presented below.

A processor-based system can include a main memory, preferably random access memory (RAM), and can also include a secondary memory. The secondary memory can include, for example, a hard disk drive and/or a removable storage drive, e.g., a floppy disk drive, a magnetic tape drive, or an optical disk drive. The removable storage drive reads from and/or writes to a removable storage medium. The removable storage medium can be a floppy disk, magnetic tape, optical disk, or the like, which is read by and written to by a removable storage drive. As will be appreciated, the removable storage medium can comprise computer software and/or data.

In alternative embodiments, the secondary memory may include other similar means for allowing computer programs or other instructions to be loaded into a computer system. Such means can include, for example, a removable storage unit and an interface. Examples can include a program cartridge and cartridge interface (such as the found in video game devices), a removable memory chip (such as an EPROM or PROM) and associated socket, and other removable storage units and interfaces, which allow software and data to be transferred from the removable storage unit to the computer system.

The computer system can also include a communications interface. Communications interfaces allow software and data to be transferred between the computer system and external devices. Examples of communications interfaces include a modem, a network interface (such as, for example, an Ethernet card), a communications port, a PCMCIA slot and card, and the like. Software and data transferred via a communications interface are in the form of signals, which can be electronic, electromagnetic, optical, or other signals capable of being received by a communications interface. These signals are provided to a communications interface via a channel capable of carrying signals and can be implemented using a wireless medium, wire or cable, fiber optics or other communications medium. Some examples of a channel include a phone line, a cellular phone link, an RF link, a network interface, and other communications channels.

In this document, the terms "computer program medium" and "computer usable medium" are used to refer generally to media such as a removable storage device, a disk capable of installation in a disk drive, and signals on a channel. These computer program products are means for providing software or program instructions to a computer system.

Computer programs (also called computer control logic) are stored in main memory and/or secondary memory. Computer programs can also be received via a communications interface. Such computer programs, when executed, enable the computer system to perform the features of the methods discussed herein. In particular, the computer programs, when executed, enable the processor to perform the features of the invention. Accordingly, such computer programs represent controllers of the computer system.

In an embodiment where the elements are implemented using software, the software may be stored in, or transmitted via, a computer program product and loaded into a computer system using a removable storage drive, hard drive, or communications interface. The control logic (software), when executed by the processor, causes the processor to perform the functions of the methods described herein.

In another embodiment, the elements are implemented primarily in hardware using, for example, hardware components such as PALs, application specific integrated circuits (ASICs) or other hardware components. Implementation of a hardware state machine so as to perform the functions described herein will be apparent to person skilled in the relevant art(s). In other embodiments, elements are implanted using a combination of both hardware and software.

In another embodiment, the computer-based methods can be accessed or implemented over the World Wide Web by providing access via a Web Page to the methods of the invention. Accordingly, the Web Page is identified by a Universal Resource Locator (URL). The URL denotes both the server machine and the particular file or page on that machine. In this embodiment, it is envisioned that a consumer or client computer system interacts with a browser to select a particular URL, which in turn causes the browser to send a request for that URL or page to the server identified in the URL. Typically the server responds to the request by retrieving the requested page and transmitting the data for that page back to the requesting client computer system (the client/server interaction is typically performed in accordance with the hypertext transport protocol ("HTTP")). The selected page is then displayed to the user on the client's display screen. The client may then cause the server containing a computer program of the invention to launch an application to, for example, perform an analysis according to the invention.

EXAMPLES

The invention is further described in the following examples, which serve to illustrate, but not to limit, the scope of the invention described in the claims.

Example 1—SHBG and P1GF Assays

Study Population and Data Acquisition

A prospective nested case-control study of patients who had enrolled in the Massachusetts General Hospital Obstetrical Maternal Study (MOMS) was performed. In brief, the MOMS cohort was established in 1998 for the prospective study of early gestational risk factors for adverse outcomes that occur later in pregnancy. For this study, consecutive women with singleton gestations between Jun. 1, 2001 and May 1, 2003 who enrolled in the MOMS cohort at approximately 12 weeks of gestation, and who delivered after 20 weeks were eligible for inclusion. All subjects provided written informed consent.

The electronic medical record, which is the medical record used by the clinical staff, provides clinical and demographic data that prospectively details the events of pregnancy through the early postpartum period. Specific information obtained from the electronic medical record included age, race, height, weight, blood pressure collected throughout gestation, fetal gestational age and weight at delivery, pregnancy outcome and laboratory values, including results of glucose tolerance tests. All subjects for the current study had no history of preexisting hypertension or diabetes mellitus, initiated and completed their prenatal care and pregnancy within our network, delivered a live infant, and had no evidence of hypertension within the ensuing 6 weeks following delivery.

Exposures

Assays for SHBG and PlGF are carried out on blood samples, serum samples or urine samples from pregnant women, as early as the first trimester, e.g., in the first 5, 6, 7, 8, 9, 10, 11, or 12 weeks of pregnancy. After providing informed written consent, eligible women had their serum samples collected at the first prenatal visit, samples were stored on ice for less than 3 hours, and then frozen at −80° C. for future analysis. The primary exposures were serum sex hormone binding globulin (SHBG), placental growth factor (PlGF), and sFlt1 (soluble inhibitor of VEGF and PlGF). Serum levels of VEGF are undetectable early in pregnancy. The present study focused on serum levels of PlGF, which is a VEGF-like molecule with proangiogenic properties and which binds to and activates the VEGF receptor Flt1. Low levels of SHBG have been associated with insulin resistance in both the pregnant and non-pregnant states. In the present methods, SHBG can be measured in either fasting or non-fasting state. Sex hormone binding globulin was measured using an immunoradiometric assay (Diagnostic Products Corporation, California USA) that has an intra-assay coefficient of variation (CV) <4%, and an inter-assay CV <7.8%. The sensitivity of the SHBG assay is 2 nmol/L. Commercial assay ELISA kits for sFlt1 and free PlGF (R&D systems, Minnesota USA) were used as previously described 2. The intra-assay precision CV (%) for sFlt1 and PlGF were 3.5 and 5.6, respectively. The inter-assay precision CV (%) for sFlt1 and PlGF were 8.1 and 10.9, respectively. All samples were run in duplicate, and if >10% variation existed between duplicates, the assay was repeated and averages reported. The corresponding laboratory was blinded to case status, and all samples were randomly ordered.

Outcomes

All pregnancy outcomes were prospectively examined and verified by detailed examination of medical records including prenatal flow sheets and laboratory investigations. Eligible cases were consecutively identified during the study period. Preeclampsia was defined as systolic blood pressure elevation 140 or diastolic blood pressure 90 mm Hg after 20 weeks of gestation, in association with proteinuria, either $^3$2+ by dipstick or $^3$300 mg/24 hours in the absence of urinary tract infection. Controls (~2:1) were randomly selected from women who participated in the MOMS cohort within the same time period as cases, delivered appropriate for gestational age infants, and remained normotensive and non-proteinuric throughout pregnancy. Women with a history of diabetes, thyroid, liver, or chronic renal disease, or preexisting chronic hypertension (defined as blood pressure >140/90 or need for anti-hypertensive medications prior to pregnancy or before 20 weeks gestation) were excluded, as were all women who failed the initial glucose loading test that is typically administered in the early third trimester of gestation.

Statistical Analysis

Continuous variables were analyzed by student's t-test, and categorical variables were analyzed by the chi square test. Primary exposures—PlGF, sFlt1, and SHBG—were examined as continuous variables, and as binomial variables with cut points based on the 25th percentile levels in the controls. Multivariable analysis was performed using logistic regression techniques, and standard tests for effect modification (interaction) including stratified models were performed. Given the strong association between first trimester serum levels of PlGF and risk for PE 3, the goal of the analysis was to determine whether the risk based on first trimester levels of PlGF was different among women with varying degrees of insulin resistance based on serum levels of SHBG. All p values were two-tailed, and a p value of <0.05 was considered statistically significant. PlGF, sFlt, and SHBG levels can be cross-correlated with: 1) the gestational age at the time the proteins are measured (ga-pnv); 2) a women's age (Mat age); 3) her parity (par); and 4) her body mass index (bmi). Tables 1-3 and FIG. 1 provide epidemiological evidence for predicting a gestational disorder based on multivariate modeling.

TABLE 1

|  | Preeclampsia (n = 28) | Normotensive Control (n = 57) |
|---|---|---|
| Baseline Characteristic |  |  |
| Age (yrs) | 31 ± 5 | 30 ± 6 |
| Gestational Age First Prenatal Visit (weeks) | 11 ± 2 | 12 ± 3 |
| Caucasian Race (%) | 64 | 45 |
| Nulliparous (%) | 60* | 25 |
| Body Mass Index (kg/m$^2$) | 26.8 ± 5.4 | 25.2 ± 4.6 |
| Systolic Blood Pressure (mm Hg) | 114 ± 8* | 109 ± 10 |

TABLE 1-continued

|  | Preeclampsia (n = 28) | Normotensive Control (n = 57) |
|---|---|---|
| Delivery Characteristics |  |  |
| Gestational Age at Delivery (weeks) | 37.7 ± 2.7* | 39.6 ± 1.2 |
| Fetal Birth Weight (grams) | 3113 ± 835* | 3482 ± 460 |

Table 1 shows that baseline characteristics of women who developed preeclampsia and normotensive controls (* indicates that P<0.05).

TABLE 2

|  | Preeclampsia (n = 28) | Normotensive Controls (n = 57) |
|---|---|---|
| Placental Growth Factor (pg/ml) | 18 ± 14* | 65 ± 150 |
| sFlt1 (pg/ml) | 1032 ± 686 | 938 ± 491 |
| Sex Hormone Binding Globulin (nmol/L) | 208 ± 116† | 256 ± 101 |

Table 2 shows first trimester serum levels of placental growth factor, sFlt1, and SHBG in women who developed Preeclampsia compared to controls (* indicates that p<0.001 and † indicates that p=0.05).

Table 3 (below) shows a nested case-control study of 25 women who developed PE and 53 normotensive controls. Measures of angiogenesis, specifically placental growth factor and sFlt1, are adjusted for various confounding factors. All measures were made at 10-12 weeks of gestation, and markers are from measurements in blood.

TABLE 3

Risk of Preeclampsia According to First Trimester PlGF and SHBG Levels

|  | Odds Ratio | 95% Confidence Intervals |
|---|---|---|
| PlGF < 20 pg/ml |  |  |
| Unadjusted* | 6.4 | 1.4-29.5 |
| Adjusted† | 7.6 | 1.4-38.4 |
| Stratum specific estimates |  |  |
| SHBG ≦ 175 mg/dl PlGF < 20 pg/ml‡ | 25.5 | 0.32-119.2 |
| SHBG > 175 mg/dl PlGF < 20 pg/ml‡ | 1.8 | 0.4-15.1 |
| Multivariable model¶ SHBG ≦ 175 mg/dl |  |  |
| PlGF < 20 pg/ml | 15.1 | 1.7-134.9 |
| PlGF ≧ 20 pg/ml | 4.1 | 0.45-38.2 |
| SHBG > 175 mg/dl |  |  |
| PlGF < 20 pg/ml | 8.7 | 1.2-60.3 |
| PlGF ≧ 20 pg/ml | 1.0 | Ref |

*Referent group, PlGF ≧ 20 pg/ml
†Multivariable model adjusted for maternal age, gestational age of blood collection, race, parity, body mass index, systolic blood pressure, smoking history, serum levels of sFlt-1, and SHBG
‡Referent group is PlGF ≧ 20 pg/ml
¶Multivariable model adjusted for maternal age, gestational age of blood collection, race, parity, body mass index, systolic blood pressure, smoking history, and serum levels of sFlt-1

The data in Table 3 and FIG. 1 indicate that the metabolic syndrome and insulin resistance (characterized by measures of insulin resistance including elevated insulin levels, altered glucose levels, a marker of this syndrome namely low levels of SHBG, elevated lipid levels, elevated body mass index, elevated inflammatory markers, and altered clotting factors) interacts epidemiologically and biologically with angiogenesis factors to confer increased risk of Preeclampsia and related diseases, including risk of cardiovascular disease and diabetes.

Example 2—Cytokine Assays

The present invention demonstrates that the alteration of a single cytokine or growth factor can be used to identify subjects having, or predisposed to having, preeclampsia, GDM or GH. Urine, plasma, and serum samples were tested for cytokine levels using a cytokine array (Zyomyx®). The array permits the quantitative analysis of 30 cytokines and chemokines, including IL-1α, IL-3, IL-6, IL-10, IL-12 (p70), TNF-α, MCP-1, CD95 (sFas), IP-10, GM-CSF, IL-1β, IL-4, IL-7, IL-12 (p40), IL-13, TNF- β, MCP-3, MIG, CD23, GCSF, IL-2, IL-5, IL-8, IL-12 (p40/p70), IL-15, Eotaxin, TRAIL, sICAM-1, TGF-β and IFN-γ, using a sample volume of approximately 40 µl of complex biological fluids, such as serum or urine. The data quality is comparable to standards established by ELISA assays. A spike/recovery analysis in urine was carried out and recovery of cytokines in urine (r=0.92) was determined. All subjects had normal renal function, thus it was unlikely that urea interfered with the analysis.

Samples from 5 women who developed preeclampsia and 5 controls with normotensive pregnancies were examined for cytokine levels. In all subjects urine was collected at 16-18 weeks of pregnancy, almost 20 weeks before the clinical diagnosis of gestational disorders. These samples were collected, sorted, and stored at 80° C. until the analyses was performed. The data presented in FIG. 2 show the cytokine array pattern in serum, plasma, and urine from 5 women who subsequently developed PE and 5 women with normotensive pregnancies. All women were nulliparous. Cytokine quantification was carried out with standard calibration techniques using fluorescence intensity.

The heat map of the cytokine array in urine, serum, and plasma shown in FIG. 2 demonstrates that among women who developed preeclampsia ("subject" or "cases"), IL-6 is elevated and IL-8 is reduced (see white circle) in the urine at 16-18 weeks of gestation compared to women who had a normotensive pregnancy ("reference" or "control") and with urine samples collected at the same time. This is the first time an array of cytokines was measured in urine by this sensitive technique and the first time differences were seen in urine at this early stage of pregnancy.

FIG. 2 also demonstrates that at 16 weeks of gestation the levels of another chemokine, MCP-1, were elevated in the urine of cases as compared to controls. All protein measurements were normalized for urine creatinine concentrations.

The urine samples were further tested to determine whether or not the addition of a standard protease inhibitor (Complete MINI™, Roche) would markedly improve cytokine recovery. As shown if FIG. 3, five urine samples were tested with (+I) and without addition of the inhibitor at the time of collection. Log transformed (pg/ml) protein profiles (all samples done in duplicate) are shown. As indicated, the recovery of cytokines does not consistently increase in the presence of protease inhibitors. Furthermore, even among samples with elevated cytokine concentrations, there does not appear to be a deterioration of recovery. Finally, reproducibility studies using the cytokine chip were also performed (FIG. 4). These results indicate that the reproducibility of urine cytokine assays is excellent.

Example 3—Growth Factor Assays

In conjunction with cytokine levels, the present studies provide information regarding the levels of growth factors in urine and blood samples. Serum and urine samples from 16 weeks of gestation in 15 subjects (5 who developed GDM, 5 PE, and 5 controls) were tested with commercially available ELISA kits for exemplary growth factors sFlt-1, free-VEGF, and free-PlGF (R&D Systems). These ELISA kits have inter-assay and intra-assay CV's of <10%. All assays were performed in duplicate, and the averages are reported in FIGS. 5 and 6. Free-VEGF levels were undetectable, consistent with low VEGF levels generally detected at term.

The data derived from serum samples shown in FIG. 5 indicates that, compared to control women, women who develop GDM have low free PlGF and slightly elevated sFlt-1 levels at 16 weeks of gestation. Moreover, women who subsequently develop PE have even lower free PlGF and higher sFlt-1 levels at this same time period. The balance of anti- to pro-angiogenic factors, reflected by the ratio of sFlt-1/PlGF, differs even at 16 weeks of gestation. The data derived from urine samples is shown in FIG. 6. Since SFlt-1 is not secreted into urine due to its large size, free PlGF was targeted for identification in the urine sample. Urine cytokine levels were compared with urine PlGF levels. The data in FIG. 6 demonstrates that in general, low free-PlGF levels and elevated IL-6 and MCP-1 levels were strongly associated with subsequent PE.

FIG. 7 presents data on serum samples of women with a history of GDM (n=5), PE (n=5), and normoglycemic/normotensive uncomplicated pregnancy (UP) (n=5) 12±3 months after the incident pregnancy. These data indicate atherogenic and metabolic alterations are present among women with a history of GDM and PE, when compared to women with UP. Importantly, the elevation of CRP and IL-6 suggests persistent subclinical inflammation, and measures of increased insulin resistance (elevated HOMA-IR) and poor insulin secretion (low $\Delta I_{30}/\Delta G_{30}$) suggest increased risk for future type 2 diabetes mellitus. Both features are associated with elevated cytokine levels. In addition, IL-6 and TNF-α levels of these same women (GDM v. UP) at 16 weeks of gestation and found that serum IL-6 (GDM 1.7 pg/ml vs. 1.1 pg/ml) and TNF-α (4.37 pg/ml vs. 3.07 pg/ml), and urine IL-6 (GDM 4.24 pg/gCr vs. 1.34 pg/gCr) levels differed. These data indicate that cytokine alterations precede GDM and persist postpartum.

Example 4—IL-6, MCP-1, and IL-8 Assays

The present studies show that differences in urine IL-6 (and serum and urine MCP-1 and urine IL-8) levels at 16 weeks of gestation among women who later developed PE (or GDM) are detectable. In contrast, previous studies have failed to detect such differences (Djurovic et al., BJOG, 109:759, 2002). As described in Example 2 and shown in FIG. 2, samples from 5 women who developed preeclampsia and 5 controls with normotensive pregnancies were examined for cytokine levels in a urine sample. In all subjects urine was collected at 16-18 weeks of pregnancy, almost 20 weeks before the clinical diagnosis. Using this data, the mean levels of specific proteins at 16 weeks of gestation and postpartum were compared. The differences between means (Δ), fraction of the standard deviation this represented, and p values are shown in Table 4 (below).

TABLE 4

Urine Cytokines Intrapartum (cases vs. controls)

GDM

| | | |
|---|---|---|
| IL-6: | 4.2 vs 1.3 pg/gCr | (Δ 1.2 × SD, p = 0.09); |
| IL-1β: | 1.2 vs 0.7 pg/gCr | (Δ 0.87 × SD, p = 0.27); |

PE

| | | |
|---|---|---|
| IL-6: | 3.6 vs 1.3 pg/gCr | (Δ 1 × SD, p = 0.13); |
| IL-8: | 106.2 vs 3.9 pg/ml | (Δ 0.94 × SD, p = 0.18); |
| MCP1: | 494 vs 244 pg/gCr | (Δ 1.1 × SD, p = 0.08); |
| PlGF: | 53.7 vs 71.9 pg/gCr | (Δ 0.89 × SD, p = 0.22). |

Serum Cytokines (cases vs. controls):

GDM

| | | |
|---|---|---|
| IL-6 (postpartum): | 2.1 vs 1.1 pg/ml | (Δ 0.98 × SD, p = 0.15); |
| TNF-α (intrapartum): | 4.37 vs 3.07 pg/ml | (Δ 0.88 × SD, p = 0.21); |

PE

| | | |
|---|---|---|
| sFlt-1 intrapartum: | 1176 vs 478 pg/m | (Δ 0.99 × SD, p = 0.12); |
| PlGF intrapartum: | 26 vs. 163 pg/ml | (Δ 1.14 × SD, p = 0.08). |

The power (1-β) for detecting mean differences was estimated with standard deviations that differ by 0.75, 1.0, and 1.25 (based on two-sample, two-sided t-tests with a conservative Bonferonni adjusted p of 0.05/8, or 0.006 for 8 pre-specified cytokines) and 1:1 cases:controls. The results are shown in FIG. 10. The data indicate that 60 cases and 60 controls provides at least 90% power to detect a difference in means separated by 0.75 standard deviation or greater. FIG. 11 is a table providing the results of a calculation that detects significant linear trends (chi-square test for trend) across tertiles for identifying the relative risk (RR) of a subject in developing a gestational disorder.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining whether a pregnant subject has, or is predisposed to having, preeclampsia, the method comprising:
   a) measuring a level of sex hormone binding globulin (SHBG) in a biological sample comprising serum or blood obtained from a pregnant subject;
   b) measuring a level of placental growth factor (PlGF) in a biological sample comprising serum or blood obtained from the pregnant subject;
   c) comparing the SHBG level obtained from the pregnant subject with a reference SHBG level obtained from at least one subject having a normal pregnancy; and
   d) comparing the PlGF level obtained from the pregnant subject with a reference PlGF level obtained from at least one subject having a normal pregnancy, wherein low levels of SHBG and PlGF present in the sample obtained from the pregnant subject, as compared to the levels present in the at least one subject having a normal pregnancy, indicate that the pregnant subject has, or is predisposed to having, a gestational disorder.

2. The method of claim 1, wherein the samples are obtained from the pregnant subject at about 9 to 13 weeks of gestation.

3. The method of claim 1, wherein the samples obtained from the pregnant subject and the subject having a normal pregnancy are obtained during the same week of pregnancy, plus or minus 2 weeks.

4. The method of claim 1, wherein the samples obtained from the pregnant subject and the subject having a normal pregnancy are each obtained during the same week of pregnancy.

5. The method of claim 1, further comprising correlating the SHBG and PlGF levels derived from the pregnant subject with: 1) the gestational age at the time SHBG and PlGF levels are measured; 2) the pregnant subject's age; 3) the pregnant subject's parity; and 4) the pregnant subject's body mass index.

6. The method of claim 1, wherein the level of SHBG and the level of PlGF in the sample obtained from the pregnant subject are measured with two or more different biomolecules, wherein a first biomolecule specifically interacts with SHBG and a second biomolecule specifically interacts with PlGF.

7. The method of claim 6, further comprising preparing a subject profile by detecting a modification of the biomolecules, wherein the modification is indicative of a level of SHBG and PlGF in the sample; and comparing the subject profile with a reference profile, wherein the reference profile comprises one or more values, each value representing a level of SHBG and PlGF in a reference sample obtained from one or more reference subjects having a normal pregnancy; wherein lower levels of SHBG and PlGF in the subject profile as compared to the reference profile is indicative of a subject having, or predisposed to having, a gestational disorder.

8. The method of claim 6, wherein the biomolecules are immobilized to form an array.

9. The method of claim 8, wherein the array comprises a first set of a plurality of the first biomolecule and a second set of a plurality of the second biomolecule.

10. The method of claim 6, wherein the biomolecules are antibodies.

11. The method of claim 10, wherein the antibodies are monoclonal antibodies.

12. The method of claim 6, wherein the biomolecules are antigens.

13. The method of claim 12, wherein the antigens are viral antigens.

14. The method of claim 6, wherein the biomolecules are receptors.

15. The method of claim 7, wherein the modification is binding of SHBG or PlGF to a biomolecule.

* * * * *